(12) United States Patent
Kim et al.

(10) Patent No.: US 8,513,277 B2
(45) Date of Patent: Aug. 20, 2013

(54) PYRROLO[3,2-C] PYRIDINE DERIVATIVES AND PROCESSES FOR THE PREPARATION THEREOF

(75) Inventors: Jae-Gyu Kim, Seoul (KR); Byung-Nak Ahn, Seoul (KR); Hyouk-Woo Lee, Yongin (KR); Suk-Won Yoon, Seoul (KR); Young-Ae Yoon, Seoul (KR); Dong-Hoon Kim, Gunpo (KR); Se-Hoon Keum, Seoul (KR); Young-Ah Shin, Yongin (KR); Heui Il Kang, Gunpo (KR); Ryong Choi, Suwon (KR); Sun-Young Jang, legal representative, Suwon (KR)

(73) Assignee: Yuhan Corporation, Seoul (KR)

( * ) Notice: Subject to any disclaimer, the term of this patent is extended or adjusted under 35 U.S.C. 154(b) by 51 days.

(21) Appl. No.: 13/296,378

(22) Filed: Nov. 15, 2011

(65) Prior Publication Data

US 2012/0065224 A1  Mar. 15, 2012

Related U.S. Application Data

(62) Division of application No. 11/574,393, filed as application No. PCT/KR2005/002924 on Sep. 3, 2005, now Pat. No. 8,148,529.

(30) Foreign Application Priority Data

Sep. 3, 2004 (KR) .................. 10-2004-0070536

(51) Int. Cl.
| A61K 31/4709 | (2006.01) |
| A61P 29/00 | (2006.01) |
| A61P 1/04 | (2006.01) |
| A61P 1/00 | (2006.01) |
| C07D 471/04 | (2006.01) |

(52) U.S. Cl.
USPC .......................... 514/300; 546/113

(58) Field of Classification Search
USPC .......................... 514/300; 546/113
See application file for complete search history.

(56) References Cited

U.S. PATENT DOCUMENTS

| 4,450,164 A | 5/1984 | Bristol et al. |
| 2004/0110785 A1 | 6/2004 | Wang et al. |

FOREIGN PATENT DOCUMENTS

| EP | 775120 | 2/1996 |
| WO | WO 98/28322 A1 | 8/1998 |
| WO | WO 99/28322 A1 | 6/1999 |
| WO | 9937304 | * 7/1999 |
| WO | WO 00/017200 A1 | 3/2000 |
| WO | WO 03/009852 A1 | 2/2003 |

OTHER PUBLICATIONS

Casy et al., "4-Substituted-1-methyl-1H-pyrrolo[3,2-c]pyridines," J. Chem. Research, Synopses, 1986, p. 4.
Ducrocq et al., Aza-Indoles-III Synthesis de l'Amino-4, AZA-5 Indole et Du N-5 Ribonucleoside Correspondant (Iso-Deaza-1 Tubercidine), Tetrahedron, 1976, 32(7), pp. 773-780.
European Patent Office Extended Search Report in EP Application No. 05781131.7, mailed Nov. 19, 2009.
Girgis et al., "The synthesis of 5-azaindoles by substitution-rearrangement of 7-azaindoles upon treatment with certain primary amines," J. of Heterocyclic Chemistry, 1989, 26(2), pp. 317-325.
Litchfield et al., "A Simplified Method of Evaluating Dose-Effect Experiments," J. Pharmacol. Exp. Ther., 1949, vol. 96, p. 99.
Bisagni et al., New Heterocyclic Rearrangement: Transformation of 1-Substituted 4-(Alkylamino)-1H-pyrrolo[3,2-c]pyridines into 1-Substituted 4-(Alkylamino)-1H-pyrrolo[2,3-b]pyridines (5-Aza- to 7-Azaindoles), J. Org. Chem., 1982, vol. 47, pp. 1500-1503.
Japanese Patent Office, Japanese Office Action issued in corresponding JP Application No. 2007-529714, dated Apr. 24, 2012.

* cited by examiner

*Primary Examiner* — Niloofar Rahmani
(74) *Attorney, Agent, or Firm* — Sughrue Mion, PLLC

(57) ABSTRACT

The present invention provides novel pyrrolo[3,2-c]pyridine derivatives or pharmaceutically acceptable salts thereof, processes for the preparation thereof, and compositions comprising the same. The pyrrolo[3,2-c]pyridine derivatives or pharmaceutically acceptable salts thereof of the present invention have excellent proton pump inhibition effects and possess the ability to attain a reversible proton pump inhibitory effect.

5 Claims, No Drawings

PYRROLO[3,2-C] PYRIDINE DERIVATIVES AND PROCESSES FOR THE PREPARATION THEREOF

This application is a divisional application of U.S. application Ser. No. 11/574,393 filed on Jun. 13, 2008, which is a national stage application under 35 U.S.C. §371 of PCT/KR2005/002924 filed on Sep. 3, 2005, which claims priority from Korean patent application 10-2004-0070536 filed on Sep. 3, 2004, all of which are incorporated herein by reference.

FIELD OF THE INVENTION

The present invention relates to novel pyrrolo[3,2-c]pyridine derivatives or pharmaceutically acceptable salts thereof which have an excellent inhibitory activity against gastric acid secretion, processes for the preparation thereof, and pharmaceutical compositions comprising the same.

BACKGROUND OF THE INVENTION

Peptic ulcer disease occurs when offensive factors involving gastric acid secretion are strong or defensive factors of gastric mucous are weak. For the treatment of peptic ulcer disease, various drugs such as antacid, anticholinergic agent, $H_2$-receptor antagonist, and proton pump inhibitor have been used. The advent of omeprazole as a proton pump inhibitor has rekindled research activities in this field.

However, it has been pointed out that proton pump inhibition by omeprazole is irreversible, thereby incurring long-term inhibition of gastric acid secretion, which may induce side effects. Accordingly, various attempts to develop a reversible proton pump inhibitor are being made. For example, imidazopyridine derivatives are disclosed in WO 98/37,080 (AstraZeneca AB), WO 00/17,200 (Byk Gulden Lomberg Chem.), and U.S. Pat. No. 4,450,164 (Schering Corporation) as a reversible proton pump inhibitor. Further, pyrimidine derivatives are also disclosed in European Patent No. 775,120 (Yuhan Corp.).

DISCLOSURE OF THE INVENTION

The present invention provides novel pyrrolo[3,2-c]pyridine derivatives or pharmaceutically acceptable salts thereof, which have excellent proton pump inhibition effects and possess the ability to attain a reversible proton pump inhibitory effect.

According to an aspect of the present invention, there is provided a pyrrolo[3,2-c]pyridine derivative or a pharmaceutically acceptable salt thereof.

Further, according to another aspect of the present invention, there is provided a process for the preparation of the pyrrolo[3,2-c]pyridine derivative or a pharmaceutically acceptable salt thereof.

Further, according to another aspect of the present invention, there is provided a pharmaceutical composition comprising the pyrrolo[3,2-c]pyridine derivative or a pharmaceutically acceptable salt thereof as an active ingredient and a pharmaceutically acceptable carrier.

BEST MODE FOR CARRYING OUT THE INVENTION

In accordance with an aspect of the present invention, there is provided a compound of the formula (I) or a pharmaceutically acceptable salt thereof:

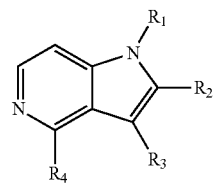

wherein:
$R_1$ is hydrogen; a straight or branched $C_1$-$C_6$ alkyl group, optionally substituted with one or more substituents selected from the group consisting of $C_1$-$C_5$ alkoxy, hydroxy, $C_3$-$C_7$ cycloalkyl, $C_1$-$C_3$ alkyl-thiazolyl, and 1,3-dioxolanyl; a straight or branched $C_2$-$C_6$ alkenyl group; a straight or branched $C_2$-$C_6$ alkynyl group; a $C_3$-$C_7$ cycloalkyl group; or a benzyl group, optionally substituted with one or more substituents selected from the group consisting of halogen, $C_1$-$C_3$ alkyl, and $C_1$-$C_3$ alkoxy,
$R_2$ is hydrogen or a straight or branched $C_1$-$C_6$ alkyl group,
$R_3$ is hydrogen; a straight or branched $C_1$-$C_6$ alkyl group; a straight or branched $C_2$-$C_6$ alkenyl group; or a benzyl group optionally one or more substituted with halogen, and
$R_4$ is a 1,2,3,4-tetrahydroisoquinolinyl group; a benzyloxy group optionally one or more substituted with halogen; or an amino group substituted with one or two substituents selected from the group consisting of hydrogen, straight or branched $C_1$-$C_5$ alkylcarbonyl, phenoxycarbonyl, benzyl optionally one or more substituted with halogen, and benzoyl optionally one or more substituted with halogen.

Among the compounds of the formula (I) or its pharmaceutically acceptable salt of the present invention, preferred are those wherein:
$R_1$ is hydrogen; a straight or branched $C_1$-$C_6$ alkyl group; a $C_1$-$C_3$ alkyl group substituted with one or more substituents selected from the group consisting of methoxy, ethoxy, hydroxy, cyclopropyl, cyclobutyl, cyclohexyl, methylthiazolyl, and 1,3-dioxolanyl; a straight or branched $C_2$-$C_6$ alkenyl group; a straight or branched $C_2$-$C_6$ alkynyl group; cyclopropyl; cyclopentyl; or a benzyl group, optionally substituted with one or more substituents selected from the group consisting of halogen, methyl, and methoxy,
$R_2$ is a straight or branched $C_1$-$C_3$ alkyl group,
$R_3$ is hydrogen; a straight or branched $C_1$-$C_3$ alkyl group; a straight or branched $C_2$-$C_5$ alkenyl group; or a benzyl group optionally one or more substituted with halogen, and
$R_4$ is a 1,2,3,4-tetrahydroisoquinolinyl group; a benzyloxy group optionally one or more substituted with halogen; or an amino group substituted with one or two substituents selected from the group consisting of hydrogen, straight or branched $C_1$-$C_5$ alkylcarbonyl, phenoxycarbonyl, benzyl optionally one or more substituted with halogen, and benzoyl optionally one or more substituted with halogen.

More preferred compounds of the formula (I) or its pharmaceutically acceptable salts of the present invention are:
2,3-dimethyl-4-(1,2,3,4-tetrahydroisoquinolin-2-yl)-1H-pyrrolo[3,2-c]pyridine;
2,3-dimethyl-4-(1,2,3,4-tetrahydroisoquinolin-2-yl)-1H-pyrrolo[3,2-c]pyridine hydrochloride;
2,3-dimethyl-1-(2-methoxyethyl)-4-(1,2,3,4-tetrahydroisoquinolin-2-yl)-1H-pyrrolo[3,2-c]pyridine hydrochloride;
1-allyl-2,3-dimethyl-4-(1,2,3,4-tetrahydroisoquinolin-2-yl)-1H-pyrrolo[3,2-c]pyridine hydrochloride;
1-benzyl-2,3-dimethyl-4-(1,2,3,4-tetrahydroisoquinolin-2-yl)-1H-pyrrolo[3,2-c]pyridine hydrochloride;

1,2,3-trimethyl-4-(1,2,3,4-tetrahydroisoquinolin-2-yl)-1H-pyrrolo[3,2-c]pyridine hydrochloride;
1-ethyl-2,3-dimethyl-4-(1,2,3,4-tetrahydroisoquinolin-2-yl)-1H-pyrrolo[3,2-c]pyridine hydrochloride;
1-propyl-2,3-dimethyl-4-(1,2,3,4-tetrahydroisoquinolin-2-yl)-1H-pyrrolo[3,2-c]pyridine hydrochloride;
1-butyl-2,3-dimethyl-4-(1,2,3,4-tetrahydroisoquinolin-2-yl)-1H-pyrrolo[3,2-c]pyridine hydrochloride;
2,3-dimethyl-1-isopropyl-4-(1,2,3,4-tetrahydroisoquinolin-2-yl)-1H-pyrrolo[3,2-c]pyridine hydrochloride;
2,3-dimethyl-1-isobutyl-4-(1,2,3,4-tetrahydroisoquinolin-2-yl)-1H-pyrrolo[3,2-c]pyridine hydrochloride;
2,3-dimethyl-1-(3-methylbutyl)-4-(1,2,3,4-tetrahydroisoquinolin-2-yl)-1H-pyrrolo[3,2-c]pyridine hydrochloride;
2,3-dimethyl-1-cyclopropyl-4-(1,2,3,4-tetrahydroisoquinolin-2-yl)-1H-pyrrolo[3,2-c]pyridine hydrochloride;
2,3-dimethyl-1-cyclopentyl-4-(1,2,3,4-tetrahydroisoquinolin-2-yl)-1H-pyrrolo[3,2-c]pyridine hydrochloride;
2,3-dimethyl-1-cyclopropylmethyl-4-(1,2,3,4-tetrahydroisoquinolin-2-yl)-1H-pyrrolo[3,2-c]pyridine hydrochloride;
1-cyclobutylmethyl-2,3-dimethyl-4-(1,2,3,4-tetrahydroisoquinolin-2-yl)-1H-pyrrolo[3,2-c]pyridine hydrochloride;
1-cyclohexylmethyl-2,3-dimethyl-4-(1,2,3,4-tetrahydroisoquinolin-2-yl)-1H-pyrrolo[3,2-c]pyridine hydrochloride;
2,3-dimethyl-1-(pent-4-ynyl)-4-(1,2,3,4-tetrahydroisoquinolin-2-yl)-1H-pyrrolo[3,2-c]pyridine hydrochloride;
2,3-dimethyl-1-(3-methylbut-2-enyl)-4-(1,2,3,4-tetrahydroisoquinolin-2-yl)-1H-pyrrolo[3,2-c]pyridine hydrochloride;
2,3-dimethyl-1-(2-hydroxyethyl)-4-(1,2,3,4-tetrahydroisoquinolin-2-yl)-1H-pyrrolo[3,2-c]pyridine hydrochloride;
2,3-dimethyl-1-methoxymethyl-4-(1,2,3,4-tetrahydroisoquinolin-2-yl)-1H-pyrrolo[3,2-c]pyridine hydrochloride;
2,3-dimethyl-1-(2-ethoxyethyl)-4-(1,2,3,4-tetrahydroisoquinolin-2-yl)-1H-pyrrolo[3,2-c]pyridine hydrochloride;
2,3-dimethyl-1-(2-methoxyethoxymethyl)-4-(1,2,3,4-tetrahydroisoquinolin-2-yl)-1H-pyrrolo[3,2-c]pyridine hydrochloride;
2,3-dimethyl-1-([1,3]dioxolan-2-ylmethyl)-4-(1,2,3,4-tetrahydroisoquinolin-2-yl)-1H-pyrrolo[3,2-c]pyridine hydrochloride;
2,3-dimethyl-1-(2-fluorobenzyl)-4-(1,2,3,4-tetrahydroisoquinolin-2-yl)-1H-pyrrolo[3,2-c]pyridine hydrochloride;
2,3-dimethyl-1-(3-fluorobenzyl)-4-(1,2,3,4-tetrahydroisoquinolin-2-yl)-1H-pyrrolo[3,2-c]pyridine hydrochloride;
2,3-dimethyl-1-(4-fluorobenzyl)-4-(1,2,3,4-tetrahydroisoquinolin-2-yl)-1H-pyrrolo[3,2-c]pyridine hydrochloride;
2,3-dimethyl-1-(4-chlorobenzyl)-4-(1,2,3,4-tetrahydroisoquinolin-2-yl)-1H-pyrrolo[3,2-c]pyridine hydrochloride;
2,3-dimethyl-1-(4-methylbenzyl)-4-(1,2,3,4-tetrahydroisoquinolin-2-yl)-1H-pyrrolo[3,2-c]pyridine hydrochloride;
2,3-dimethyl-1-(4-methoxybenzyl)-4-(1,2,3,4-tetrahydroisoquinolin-2-yl)-1H-pyrrolo[3,2-c]pyridine hydrochloride;
2,3-dimethyl-1-(2-methylthiazol-4-ylmethyl)-4-(1,2,3,4-tetrahydroisoquinolin-2-yl)-1H-pyrrolo[3,2-c]pyridine hydrochloride;
2,3-dimethyl-4-(4-fluorobenzylamino)-1H-pyrrolo[3,2-c]pyridine;
2,3-dimethyl-4-(4-fluorobenzylamino)-1H-pyrrolo[3,2-c]pyridine hydrochloride;
1,2,3-trimethyl-4-(4-fluorobenzylamino)-1H-pyrrolo[3,2-c]pyridine hydrochloride;
2,3-dimethyl-1-ethyl-4-(4-fluorobenzylamino)-1H-pyrrolo[3,2-c]pyridine hydrochloride;
2,3-dimethyl-1-propyl-4-(4-fluorobenzylamino)-1H-pyrrolo[3,2-c]pyridine hydrochloride;
1-allyl-2,3-dimethyl-4-(4-fluorobenzylamino)-1H-pyrrolo[3,2-c]pyridine hydrochloride;
2,3-dimethyl-1-isopropyl-4-(4-fluorobenzylamino)-1H-pyrrolo[3,2-c]pyridine hydrochloride;
1-isobutyl-2,3-dimethyl-4-(4-fluorobenzylamino)-1H-pyrrolo[3,2-c]pyridine hydrochloride;
1-cyclopropylmethyl-2,3-dimethyl-4-(4-fluorobenzylamino)-1H-pyrrolo[3,2-c]pyridine hydrochloride;
2,3-dimethyl-1-(2-methoxyethyl)-4-(4-fluorobenzylamino)-1H-pyrrolo[3,2-c]pyridine hydrochloride;
2,3-dimethyl-1-([1,3]dioxolan-2-ylmethyl)-4-(4-fluorobenzylamino)-1H-pyrrolo[3,2-c]pyridine hydrochloride;
1-benzyl-2,3-dimethyl-4-(4-fluorobenzylamino)-1H-pyrrolo[3,2-c]pyridine hydrochloride;
2,3-dimethyl-1-(2-fluorobenzyl)-4-(4-fluorobenzylamino)-1H-pyrrolo[3,2-c]pyridine hydrochloride;
2,3-dimethyl-1-(3-fluorobenzyl)-4-(4-fluorobenzylamino)-1H-pyrrolo[3,2-c]pyridine hydrochloride;
2,3-dimethyl-1-(4-fluorobenzyl)-4-(4-fluorobenzylamino)-1H-pyrrolo[3,2-c]pyridine hydrochloride;
7-[N-benzyl-N-(4-fluorobenzyl)]amino-1,2,3-trimethyl-1H-pyrrolo[3,2-c]pyridine hydrochloride;
7-[N,N-di-(4-fluorobenzyl)]amino-1,2,3-trimethyl-1H-pyrrolo[3,2-c]pyridine hydrochloride;
7-[N-acetyl-N-(4-fluorobenzyl)]amino-1,2,3-trimethyl-1H-pyrrolo[3,2-c]pyridine hydrochloride;
7-[N-isobutyryl-N-(4-fluorobenzyl)]amino-1,2,3-trimethyl-1H-pyrrolo[3,2-c]pyridine hydrochloride;
7-[N-benzoyl-N-(4-fluorobenzyl)]amino-1,2,3-trimethyl-1H-pyrrolo[3,2-c]pyridine hydrochloride;
7-[N-(2-chlorobenzoyl)-N-(4-fluorobenzyl)]amino-1,2,3-trimethyl-1H-pyrrolo[3,2-c]pyridine hydrochloride;
7-[N-(4-fluorobenzyl)-N-phenoxycarbonyl]amino-1,2,3-trimethyl-1H-pyrrolo[3,2-c]pyridine hydrochloride;
3-benzyl-2-methyl-4-(1,2,3,4-tetrahydroisoquinolin-2-yl)-1H-pyrrolo[3,2-c]pyridine;
3-benzyl-2-methyl-4-(1,2,3,4-tetrahydroisoquinolin-2-yl)-1H-pyrrolo[3,2-c]pyridine hydrochloride;
3-benzyl-1,2-dimethyl-4-(1,2,3,4-tetrahydroisoquinolin-2-yl)-1H-pyrrolo[3,2-c]pyridine hydrochloride;
3-benzyl-1-ethyl-2-methyl-4-(1,2,3,4-tetrahydroisoquinolin-2-yl)-1H-pyrrolo[3,2-c]pyridine hydrochloride;
3-benzyl-1-propyl-2-methyl-4-(1,2,3,4-tetrahydroisoquinolin-2-yl)-1H-pyrrolo[3,2-c]pyridine hydrochloride;
1-allyl-3-benzyl-2-methyl-4-(1,2,3,4-tetrahydroisoquinolin-2-yl)-1H-pyrrolo[3,2-c]pyridine hydrochloride;
3-benzyl-1-isobutyl-2-methyl-4-(1,2,3,4-tetrahydroisoquinolin-2-yl)-1H-pyrrolo[3,2-c]pyridine hydrochloride;
3-benzyl-1-cyclopropyl-2-methyl-4-(1,2,3,4-tetrahydroisoquinolin-2-yl)-1H-pyrrolo[3,2-c]pyridine hydrochloride;
3-benzyl-1-cyclopropylmethyl-2-methyl-4-(1,2,3,4-tetrahydroisoquinolin-2-yl)-1H-pyrrolo[3,2-c]pyridine hydrochloride;
3-benzyl-1-(2-methoxyethyl)-2-methyl-4-(1,2,3,4-tetrahydroisoquinolin-2-yl)-1H-pyrrolo[3,2-c]pyridine hydrochloride;
3-benzyl-1-(2-hydroxyethyl)-2-methyl-4-(1,2,3,4-tetrahydroisoquinolin-2-yl)-1H-pyrrolo[3,2-c]pyridine hydrochloride;
3-benzyl-1-([1,3]dioxolan-2-ylmethyl)-2-methyl-4-(1,2,3,4-tetrahydroisoquinolin-2-yl)-1H-pyrrolo[3,2-c]pyridine hydrochloride;
1,3-dibenzyl-2-methyl-4-(1,2,3,4-tetrahydroisoquinolin-2-yl)-1H-pyrrolo[3,2-c]pyridine hydrochloride;

3-benzyl-1-(2-fluorobenzyl)-2-methyl-4-(1,2,3,4-tetrahydroisoquinolin-2-yl)-1H-pyrrolo[3,2-c]pyridine hydrochloride;
3-benzyl-1-(3-fluorobenzyl)-2-methyl-4-(1,2,3,4-tetrahydroisoquinolin-2-yl)-1H-pyrrolo[3,2-c]pyridine hydrochloride;
3-benzyl-1-(4-fluorobenzyl)-2-methyl-4-(1,2,3,4-tetrahydroisoquinolin-2-yl)-1H-pyrrolo[3,2-c]pyridine hydrochloride;
3-benzyl-2-methyl-4-(1,2,3,4-tetrahydroisoquinolin-2-yl)-1H-pyrrolo[3,2-c]pyridine sodium;
3-benzyl-2-methyl-4-(4-fluorobenzylamino)-1H-pyrrolo[3,2-c]pyridine hydrochloride;
3-benzyl-1,2-dimethyl-4-(4-fluorobenzylamino)-1H-pyrrolo[3,2-c]pyridine hydrochloride;
3-benzyl-2-methyl-4-(4-chlorobenzylamino)-1H-pyrrolo[3,2-c]pyridine hydrochloride;
3-benzyl-1,2-dimethyl-4-(4-chlorobenzylamino)-1H-pyrrolo[3,2-c]pyridine hydrochloride;
3-benzyl-2-methyl-4-(4-fluorobenzyloxy)-1H-pyrrolo[3,2-c]pyridine hydrochloride;
3-benzyl-1,2-dimethyl-4-(4-fluorobenzyloxy)-1H-pyrrolo[3,2-c]pyridine hydrochloride;
3-benzyl-2-methyl-4-(4-chlorobenzyloxy)-1H-pyrrolo[3,2-c]pyridine hydrochloride;
3-benzyl-1,2-dimethyl-4-(4-chlorobenzyloxy)-1H-pyrrolo[3,2-c]pyridine hydrochloride;
3-(3-fluorobenzyl)-2-methyl-4-(1,2,3,4-tetrahydroisoquinolin-2-yl)-1H-pyrrolo[3,2-c]pyridine hydrochloride;
3-(3-fluorobenzyl)-1,2-dimethyl-4-(1,2,3,4-tetrahydroisoquinolin-2-yl)-1H-pyrrolo[3,2-c]pyridine hydrochloride;
3-allyl-2-methyl-4-(1,2,3,4-tetrahydroisoquinolin-2-yl)-1H-pyrrolo[3,2-c]pyridine hydrochloride;
3-allyl-1,2-dimethyl-4-(1,2,3,4-tetrahydroisoquinolin-2-yl)-1H-pyrrolo[3,2-c]pyridine hydrochloride.

Among them, particularly preferred compounds of the formula (I) or its pharmaceutically acceptable salts are:
2,3-dimethyl-4-(1,2,3,4-tetrahydroisoquinolin-2-yl)-1H-pyrrolo[3,2-c]pyridine;
2,3-dimethyl-4-(1,2,3,4-tetrahydroisoquinolin-2-yl)-1H-pyrrolo[3,2-c]pyridine hydrochloride;
2,3-dimethyl-1-(2-methoxyethyl)-4-(1,2,3,4-tetrahydroisoquinolin-2-yl)-1H-pyrrolo[3,2-c]pyridine hydrochloride;
1,2,3-trimethyl-4-(1,2,3,4-tetrahydroisoquinolin-2-yl)-1H-pyrrolo[3,2-c]pyridine hydrochloride;
1-ethyl-2,3-dimethyl-4-(1,2,3,4-tetrahydroisoquinolin-2-yl)-1H-pyrrolo[3,2-c]pyridine hydrochloride;
2,3-dimethyl-1-(2-hydroxyethyl)-4-(1,2,3,4-tetrahydroisoquinolin-2-yl)-1H-pyrrolo[3,2-c]pyridine hydrochloride;
3-benzyl-2-methyl-4-(1,2,3,4-tetrahydroisoquinolin-2-yl)-1H-pyrrolo[3,2-c]pyridine hydrochloride;
3-benzyl-1,2-dimethyl-4-(1,2,3,4-tetrahydroisoquinolin-2-yl)-1H-pyrrolo[3,2-c]pyridine hydrochloride;
3-benzyl-1-ethyl-2-methyl-4-(1,2,3,4-tetrahydroisoquinolin-2-yl)-1H-pyrrolo[3,2-c]pyridine hydrochloride;
3-benzyl-1-cyclopropyl-2-methyl-4-(1,2,3,4-tetrahydroisoquinolin-2-yl)-1H-pyrrolo[3,2-c]pyridine hydrochloride;
3-benzyl-1-(2-methoxyethyl)-2-methyl-4-(1,2,3,4-tetrahydroisoquinolin-2-yl)-1H-pyrrolo[3,2-c]pyridine hydrochloride;
3-benzyl-1-([1,3]dioxolan-2-ylmethyl)-2-methyl-4-(1,2,3,4-tetrahydroisoquinolin-2-yl)-1H-pyrrolo[3,2-c]pyridine hydrochloride;
1,3-dibenzyl-2-methyl-4-(1,2,3,4-tetrahydroisoquinolin-2-yl)-1H-pyrrolo[3,2-c]pyridine hydrochloride;
3-benzyl-2-methyl-4-(1,2,3,4-tetrahydroisoquinolin-2-yl)-1H-pyrrolo[3,2-c]pyridine sodium;
3-benzyl-2-methyl-4-(4-fluorobenzylamino)-1H-pyrrolo[3,2-c]pyridine hydrochloride.

The compounds of the present invention may be pharmaceutically acceptable non-toxic salt forms. The non-toxic salts may include conventional acid addition salts used in the field of anti-ulcer agents, e.g., salts originated from inorganic acid such as hydrochloric acid, hydrobromic acid, sulfuric acid, sulfamic acid, phosphoric acid, or nitric acid, and organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, p-toluenesulfonic acid, oxalic acid, or trifluoroacetic acid. Further, the non-toxic salts include conventional metal salt forms, e.g., salts originated from metal such as lithium, sodium, potassium, magnesium, or calcium. Such acid addition salts or metal salts may be prepared in accordance with any of the conventional methods.

The present invention includes, within its scope, a process for preparing a compound of formula (I) or a pharmaceutically acceptable salt thereof, in accordance with the following Scheme 1:

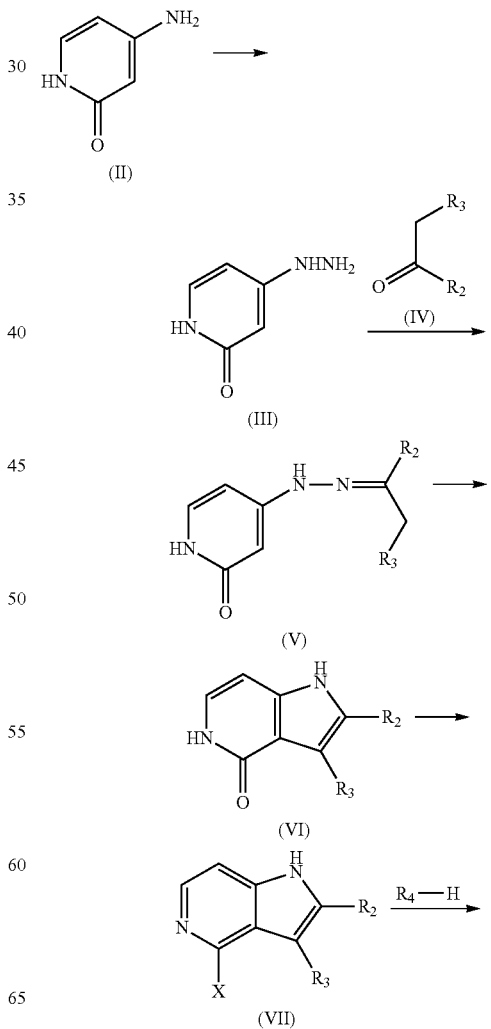

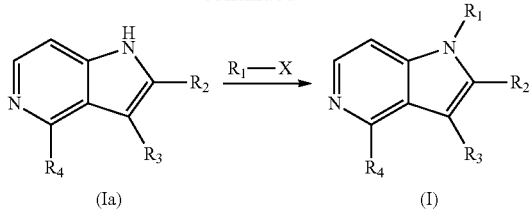

wherein, $R_1$, $R_2$, $R_3$, and $R_4$ are the same as defined in the above and X is halogen.

Specifically, the compound of formula (I) or its pharmaceutically acceptable salt may be prepared using a process which comprises: (a) adding a sodium nitrite solution to a compound of formula (II), followed by reducing the resulting product with tin chloride, to obtain a compound of formula (III); (b) reacting the compound of formula (III) with a compound of formula (IV) to obtain a compound of formula (V); (c) performing a cyclization reaction of a compound of formula (V) to obtain a compound of formula (VI); (d) halogenizing the compound of formula (VI) to obtain a compound of formula (VII); (e) reacting the compound of formula (VII) with $R_4$—H to obtain a compound of formula (Ia); and (f) reacting the compound of formula (Ia) with $R_1$—X to obtain a compound of formula (I).

In the processes of Scheme 1, the compounds of formula (II) and (IV) are commercially available. The step (a) may performed by adding a sodium nitrite solution at a temperature of −20° C.~5° C. to a solution of the compound of formula (II) in an inorganic acid, followed by reducing the resulting product with tin chloride.

A compound of formula (V) may be prepared by reacting the compound of formula (III) with a compound of formula (IV) under heating, in an organic solvent, e.g., ethanol.

The cyclization reaction of the compound of formula (V) may be performed in an organic solvent, e.g., diphenyl ether having a high boiling point. Further, the reaction may be carried out at a temperature of 100° C.~300° C.

The compound of formula (VI) is halogenized to the compound of formula (VII), using various halogenizing agents, e.g., phosphorus oxychloride. Further, the halogenizing reaction may be performed at room temperature or at a temperature of 40° C.~100° C.

The compound of formula (VII) is reacted with $R_4$—H to obtain a compound of formula (Ia). The reaction of the compound of formula (VII) and $R_4$—H may be performed in the presence of a base, such as sodium hydride, potassium tert-butoxide, sodium carbonate, or potassium hydroxide. Further, the reaction may be carried out in an organic solvent, such as tetrahydrofuran, N,N-dimethylformamide, and toluene, and at room temperature or at a temperature of 40° C.~100° C.

The compound of formula (Ia) is reacted with $R_1$—X to finally obtain a compound of formula (I). The reaction of the compound of formula (Ia) and $R_1$—X may be performed in the presence of a base, such as sodium hydride or potassium tert-butoxide. Further, the reaction may be carried out in an organic solvent, such as tetrahydrofuran or N,N-dimethylformamide, and at room temperature or at a temperature of 40° C.~100° C. In order to increase a reaction rate and/or a yield of the reaction, a catalytic amount of 18-crown-6 may be used.

The present invention further includes, within its scope, a pharmaceutical composition comprising a therapeutically effective amount of any of the compound of formula (I), as defined above, or a pharmaceutically acceptable salt thereof and a pharmaceutically acceptable carrier. The compound of formula (I) or a pharmaceutically acceptable salt thereof may be used for prevention and treatment of gastrointestinal inflammatory diseases and gastric acid-related diseases in mammals including human, such as gastritis, gastric ulcer, duodenal ulcer, reflux esophagitis and Zollinger-Ellison syndrome. Furthermore, the compounds or their salts of the present invention may be used for treatment of other gastrointestinal disorders where gastric antisecretory effect is desirable, e.g. in patients with gastrinomas, and in patients with acute upper gastrointestinal bleeding. The compounds or their salts of the present invention may also be used in patients in intensive care situations, and pre- and postoperatively to prevent acid aspiration and stress ulceration.

The composition of the present invention may include additives such as lactose or corn starch, lubricants such as magnesium stearate, emulsifiers, suspending agents, stabilizers, and isotonic agents. If necessary, sweetening agents and/or flavoring agents may be added.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral use, carriers such as lactose, corn starch, and lubricating agents, e.g. magnesium stearate, are commonly added. In the case of capsules for oral administration, lactose and/or dried corn starch can be used as a diluent. When an aqueous suspension is required for oral use, the active ingredient may be combined with emulsifying and/or suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic. The composition of the present invention may be in the form of an aqueous solution containing pharmaceutically acceptable carriers, e.g., saline, at a pH level of 7.4. The solutions may be introduced into a patient's intramuscular blood-stream by local bolus injection.

The compounds of the present invention may be administered in an effective amount ranging from about 0.1 mg/kg to about 500 mg/kg per day to a subject patient. Of course, the dosage may be changed according to the patient's age, weight, susceptibility, or symptom.

The following examples are provided for illustration purposes only, and are not intended to limit the scope of the invention.

Preparation 1.
4-chloro-2,3-dimethyl-1H-pyrrolo[3,2-c]pyridine

Step 1: 4-hydrazino-1H-pyridin-2-one 2,4-dihydroxypyridine (20.3 g, 183.0 mmol) was added to the mixture of 2-methoxyethanol (400 ml) and 55% solution of hydrazine hydrate (80 ml) at room temperature. The reaction mixture was refluxed under stirring for 24 hours and then concentrated under reduced pressure. The resulting residue was recrystallized with ethanol to give the titled compound as a white solid. (Yield: 88.3%)

TLC; methylene chloride/methanol=10/1 (v/v); Rf=0.1

¹H-NMR (CDCl₃) δ 10.30 (brs, 1H), 7.67 (s, 1H), 7.10 (d, 1H), 5.79 (d, 1H), 5.54 (s, 1H), 3.91 (brs, 2H)

Step 2: 4-(N'-sec-butyliden-hydrazino)-1H-pyridin-2-one 4-hydrazino-1H-pyridin-2-one (20.1 g, 161.0 mmol) prepared in Step 1 and 2-butanone (21.6 ml, 241.0 mmol) were added to ethanol (400 ml). The reaction mixture was refluxed under stirring for 4 hours and cooled to 0° C. The resulting precipitate was filtered and then washed with cooled ethanol to give the titled compound as a white solid. (Yield: 75.0%)
TLC; methylene chloride/methanol=10/1 (v/v); Rf=0.3
¹H-NMR (CDCl₃) δ 10.48 (brs, 1H), 9.05 (s, 1H), 7.03 (d, 1H), 6.00 (d, 1H), 5.65 (s, 1H), 2.18 (q, 2H), 1.97 (s, 3H), 0.99 (t, 3H)

Step 3: 2,3-dimethyl-1,5-dihydro-pyrrolo[3,2-c]pyridin-4-one 4-(N'-sec-butyliden-hydrazino)-1H-pyridin-2-one (16.6 g, 92.6 mmol) prepared in Step 2 was added to diphenyl ether (200 ml). The reaction mixture was refluxed under stirring for 5 hours and cooled to room temperature. n-Hexane (200 ml) was added under stirring to the reaction mixture, which was then filtered. The resulting solid was recrystallized with methanol (20 ml) to give the titled compound as a pale yellow solid. (Yield: 73.2%)
TLC; ethyl acetate (100%); Rf=0.2
¹H-NMR (CDCl₃) δ 10.99 (brs, 1H), 10.55 (brs, 1H), 6.84 (d, 1H), 6.24 (d, 1H), 2.24 (s, 3H), 2.17 (s, 3H)

Step 4: 4-chloro-2,3-dimethyl-1H-pyrrolo[3,2-c]pyridine 2,3-dimethyl-1,5-dihydro-pyrrolo[3,2-c]pyridin-4-one (6.0 g, 37.0 mmol) prepared in Step 3 was added to phosphorus oxychloride (230 ml). The reaction mixture was refluxed under stirring for 6 hours, cooled to room temperature, and then concentrated under reduced pressure. The resulting residue was dissolved in methanol (200 ml). The obtained solution was alkalized with a saturated ammonia solution in methanol and concentrated under reduced pressure. The resulting residue was purified with silica gel column chromatography (ethyl acetate) and recrystallized with ether to give the titled compound as a pale yellow solid. (Yield: 43.0%)
TLC; ethyl acetate/n-hexane=1/1 (v/v); Rf=0.4
¹H-NMR (CDCl₃) δ 11.55 (brs, 1H), 7.82 (d, 1H), 7.25 (d, 1H), 2.36 (s, 3H), 2.33 (s, 3H)

Preparation 2. 3-benzyl-4-chloro-2-methyl-1H-pyrrolo[3,2-c]pyridine

Step 1: 4-[N'-(1-methyl-3-phenyl-propylidene)-hydrazino]-1H-pyridin-2-one

In accordance with the same procedures as in Step 2 of Preparation 1, except for using 4-hydrazino-1H-pyridin-2-one (5.39 g, 43.1 mmol) prepared in Step 1 of Preparation 1 and benzylacetone (9.70 ml, 64.6 mmol), the titled compound was obtained as a white solid. (Yield: 66.5%) The product was used in the subsequent reaction without further purification.

Step 2: 3-benzyl-2-methyl-1,5-dihydro-pyrrolo[3,2-c]pyridin-4-one

In accordance with the same procedures as in Step 3 of Preparation 1, except for using 4-[N'-(1-methyl-3-phenyl-propylidene)-hydrazino]-1H-pyridin-2-one (7.30 g, 28.6 mmol) prepared in Step 1, the titled compound was obtained as a white solid. (Yield: 94%)
¹H-NMR (CDCl₃) δ 10.99 (brs, 1H), 10.55 (brs, 1H), 7.33 (m, 5H) 6.86 (d, 1H), 6.25 (d, 1H), 5.10 (s, 2H), 2.25 (s, 3H)

Step 3: 3-benzyl-4-chloro-2-methyl-1H-pyrrolo[3,2-c]pyridine

In accordance with the same procedures as in Step 4 of Preparation 1, except for using 3-benzyl-2-methyl-1,5-dihydro-pyrrolo[3,2-c]pyridin-4-one (4.82 g, 20.2 mmol) prepared in Step 2, the titled compound was obtained as a pale yellow solid. (Yield: 33%)
¹H-NMR (CDCl₃) δ 10.54 (brs, 1H), 7.32 (m, 5H), 7.12 (d, 1H), 6.28 (d, 1H), 5.11 (s, 2H), 2.28 (s, 3H)

Preparation 3. 4-chloro-3-(3-fluorobenzyl)-2-methyl-1H-pyrrolo[3,2-c]pyridine

Step 1: 4-[N'-(1-methyl-3-(3-fluorophenyl)-propylidene)-hydrazino]-1H-pyridin-2-one In accordance with the same procedures as in Step 2 of Preparation 1, except for using 4-hydrazino-1H-pyridin-2-one (5.39 g, 43.1 mmol) prepared in Step 1 of Preparation 1 and 3-fluorobenzylacetone (9.82 ml, 65.1 mmol), the titled compound was obtained as a white solid. (Yield: 63.4%) The product was used in the subsequent reaction without further purification.

Step 2: 3-(3-fluorobenzyl)-2-methyl-1,5-dihydro-pyrrolo[3,2-c]pyridin-4-one

In accordance with the same procedures as in Step 3 of Preparation 1, except for using 4-[N'-(1-methyl-3-(3-fluorophenyl)-propylidene)-hydrazino]-1H-pyridin-2-one (7.23 g, 27.7 mmol) prepared in Step 1, the titled compound was obtained as a white solid. (Yield: 88%)
¹H-NMR (CDCl₃) δ 10.87 (brs, 1H), 10.43 (brs, 1H), 7.33 (m, 3H) 7.22 (s, 1H), 6.86 (d, 1H), 6.25 (d, 1H), 5.10 (s, 2H), 2.25 (s, 3H)

Step 3: 4-chloro-3-(3-fluorobenzyl)-2-methyl-1H-pyrrolo[3,2-c]pyridine

In accordance with the same procedures as in Step 4 of Preparation 1, except for using 3-(3-fluorobenzyl)-2-methyl-1,5-dihydro-pyrrolo[3,2-c]pyridin-4-one (4.92 g, 20.9 mmol) prepared in Step 2, the titled compound was obtained as a pale yellow solid. (Yield: 32%)
¹H-NMR (CDCl₃) δ 10.43 (brs, 1H), 7.32 (m, 3H), 7.23 (s, 1H), 7.12 (d, 1H), 6.28 (d, 1H), 5.11 (s, 2H), 2.28 (s, 3H)

Preparation 4. 3-allyl-4-chloro-2-methyl-1H-pyrrolo[3,2-c]pyridine

Step 1: 4-[N'-(1-methyl-pent-4-enylidene)-hydrazino]-1H-pyridin-2-one

In accordance with the same procedures as in Step 2 of Preparation 1, except for using 4-hydrazino-1H-pyridin-2-one (5.39 g, 43.1 mmol) prepared in Step 1 of Preparation 1 and 5-hexen-2-one (7.41 ml, 64.6 mmol), the titled compound was obtained as a white solid. (Yield: 71.3%)

¹H-NMR (CDCl₃) δ 10.33 (brs, 1H), 8.94 (brs, 1H), 6.92 (d, 1H), 5.88 (d, 1H), 5.71 (m, 1H), 5.53 (s, 1H), 4.91 (d, 1H), 4.90 (d, 1H), 2.16 (m, 2+2H), 1.69 (s, 3H)

Step 2: 3-allyl-2-methyl-1,5-dihydro-pyrrolo[3,2-c]pyridin-4-one

In accordance with the same procedures as in Step 3 of Preparation 1, except for using 4-[N'-(1-methyl-pent-4-enylidene)-hydrazino]-1H-pyridin-2-one (6.87 g, 30.7 mmol) prepared in Step 1, the titled compound was obtained as a white solid. (Yield: 85%)
¹H-NMR (CDCl₃) δ 10.80 (brs, 1H), 10.22 (brs, 1H), 6.61 (d, 1H), 6.02 (d, 1H), 5.74 (m, 1H), 4.71 (d, 1H), 4.64 (d, 1H), 3.28 (d, 2H), 1.94 (s, 3H)

Step 3: 3-allyl-4-chloro-2-methyl-1H-pyrrolo[3,2-c]pyridine

In accordance with the same procedures as in Step 4 of Preparation 1, except for using 3-allyl-2-methyl-1,5-dihydro-pyrrolo[3,2-c]pyridin-4-one (4.31 g, 18.4 mmol) prepared in Step 2, the titled compound was obtained as a pale yellow solid. (Yield: 36%)
¹H-NMR (CDCl₃) δ 10.33 (brs, 1H), 6.43 (d, 1H), 6.11 (d, 1H), 5.74 (m, 1H), 4.72 (d, 1H), 4.65 (d, 1H), 3.22 (d, 2H), 1.95 (s, 3H)

Example 1

2,3-dimethyl-4-(1,2,3,4-tetrahydroisoquinolin-2-yl)-1H-pyrrolo[3,2-c]pyridine A mixture of 4-chloro-2,3-dimethyl-1H-pyrrolo[3,2-c]pyridine (1.49 g, 8.25 mmol) prepared in Preparation 1 and 1,2,3,4-tetrahydroisoquinoline (4 ml) was stirred for 12 hours at 160° C. The reaction mixture was cooled to room temperature and purified with silica gel column chromatography (ethyl acetate) to give the titled compound as a white solid. (Yield: 77.1%)
TLC; ethyl acetate (100%); Rf=0.5
¹H-NMR (CDCl₃) δ 7.65 (m, 1H), 7.37 (m, 1H), 7.17 (m, 4H), 4.69 (brs, 2H), 3.87 (brs, 2H), 3.22 (brs, 2H), 2.45 (s, 3H), 2.32 (s, 3H)

Example 2

2,3-dimethyl-4-(1,2,3,4-tetrahydroisoquinolin-2-yl)-1H-pyrrolo[3,2-c]pyridine hydrochloride 2,3-dimethyl-4-(1,2,3,4-tetrahydroisoquinolin-2-yl)-1H-pyrrolo[3,2-c]pyridine (1.83 g, 6.59 mmol) prepared in Example 1 was dissolved in ethyl acetate (10 ml). The reaction mixture was saturated with hydrochloric acid gas and then filtered to give the titled compound as a white solid. (Yield: 75.2%)
¹H-NMR (CDCl₃) δ 7.72 (m, 1H), 7.42 (m, 1H), 7.19 (m, 4H), 4.77 (brs, 2H), 3.92 (brs, 2H), 3.19 (brs, 2H), 2.46 (s, 3H), 2.30 (s, 3H)

Example 3

2,3-dimethyl-1-(2-methoxyethyl)-4-(1,2,3,4-tetrahydroisoquinolin-2-yl)-1H-pyrrolo[3,2-c]pyridine hydrochloride Sodium hydride (60%, 4.3 mg, 0.108 mmol) was added at room temperature to a solution of 2,3-dimethyl-4-(1,2,3,4-tetrahydroisoquinolin-2-yl)-1H-pyrrolo[3,2-c]pyridine (15 mg, 0.054 mmol) prepared in Example 1 in N,N-dimethylformamide (1 ml) and then the reaction mixture was stirred for 30 minutes. 2-Bromoethyl methyl ether (0.056 ml, 0.06 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 58.4%)
¹H-NMR (CDCl₃) δ 8.10 (brs, 1H), 7.23 (m, 5H), 4.83 (brs, 2H), 4.31 (brs, 2H), 4.02 (brs, 2H), 3.57 (m, 2H), 3.25 (m, 5H), 2.40 (s, 3H), 2.34 (s, 3H)

Examples 4 to 31

The titled compounds of Examples 4 to 31 were prepared, in accordance with the same procedures as in Example 3, using 2,3-dimethyl-4-(1,2,3,4-tetrahydroisoquinolin-2-yl)-1H-pyrrolo[3,2-c]pyridine prepared in Example 1; and, allyl bromide, benzyl bromide, iodomethane, iodoethane, 1-iodopropane, 1-iodobutane, 2-bromopropane, 1-bromo-2-methylpropane, 1-bromo-3-methylbutane, bromocyclopropane, bromocyclopentane, (bromomethyl)cyclopropane, (bromomethyl)cyclobutane, (bromomethyl)cyclohexane, 5-chloro-1-pentyne, 4-bromo-2-methyl-2-butene, 2-bromoethanol, bromomethyl methyl ether, 2-bromoethyl ethyl ether, 2-methoxyethoxymethyl chloride, 2-bromomethyl-1,3-dioxolane, 2-fluorobenzyl chloride, 3-fluorobenzyl chloride, 4-fluorobenzyl chloride, 4-chlorobenzyl chloride, 4-methylbenzyl chloride, 4-methoxybenzyl chloride, or 4-chloromethyl-2-methyl-thiazole.

Example 4

1-allyl-2,3-dimethyl-4-(1,2,3,4-tetrahydroisoquinolin-2-yl)-1H-pyrrolo[3,2-c]pyridine hydrochloride ¹H-NMR (CDCl₃) δ 8.11 (brs, 1H), 7.22 (m, 4H), 7.05 (brs, 1H), 5.96 (brs, 1H), 5.26 (brs, 1H), 4.80 (m, 5H), 4.05 (brs, 2H), 3.24 (brs, 2H), 2.38 (s, 3H), 2.36 (s, 3H); (Yield: 52.3%)

Example 5

1-benzyl-2,3-dimethyl-4-(1,2,3,4-tetrahydroisoquinolin-2-yl)-1H-pyrrolo[3,2-c]pyridine hydrochloride ¹H-NMR (CDCl₃) δ 8.08 (m, 1H), 7.23 (m, 7H), 7.04 (m, 1H), 6.34 (m, 2H), 5.35 (s, 2H), 4.87 (s, 2H), 4.08 (m, 2H), 3.25 (m, 2H), 2.37 (s, 3H), 2.32 (s, 3H); (Yield: 45.8%)

Example 6

1,2,3-trimethyl-4-(1,2,3,4-tetrahydroisoquinolin-2-yl)-1H-pyrrolo[3,2-c]pyridine hydrochloride ¹H-NMR (CDCl₃) δ 8.10 (m, 1H), 7.20 (m, 4H), 7.07 (m, 1H), 4.80 (s, 2H), 3.97 (m, 2H), 3.74 (s, 3H), 3.22 (m, 2H), 2.39 (s, 3H), 2.35 (s, 3H); (Yield: 69.7%)

Example 7

1-ethyl-2,3-dimethyl-4-(1,2,3,4-tetrahydroisoquinolin-2-yl)-1H-pyrrolo[3,2-c]pyridine hydrochloride $^1$H-NMR (CDCl$_3$) δ 8.11 (m, 1H), 7.20 (m, 4H), 7.07 (m, 1H), 4.82 (s, 2H), 4.18 (q, 2H), 4.02 (t, 2H), 3.23 (t, 2H), 2.39 (s, 3H), 2.34 (s, 3H), 1.39 (t, 3H); (Yield: 87.5%)

Example 8

1-propyl-2,3-dimethyl-4-(1,2,3,4-tetrahydroisoquinolin-2-yl)-1H-pyrrolo[3,2-c]pyridine hydrochloride $^1$H-NMR (CDCl$_3$) δ 8.10 (m, 1H), 7.21 (brs, 5H), 4.85 (brs, 2H), 4.09 (m, 4H), 3.24 (brs, 2H), 2.41 (s, 3H), 2.36 (s, 3H), 1.84 (brs, 2H), 1.03 (brs, 3H); (Yield: 75.3%)

Example 9

1-butyl-2,3-dimethyl-4-(1,2,3,4-tetrahydroisoquinolin-2-yl)-1H-pyrrolo[3,2-c]pyridine hydrochloride $^1$H-NMR (CDCl$_3$) δ 8.09 (m, 1H), 7.22 (brs, 5H), 4.88 (brs, 2H), 4.11 (m, 4H), 3.26 (brs, 2H), 2.39 (brs, 6H), 1.83 (brs, 2H), 1.50 (brs, 2H), 1.05 (brs, 3H); (Yield: 83.0%)

Example 10

2,3-dimethyl-1-isopropyl-4-(1,2,3,4-tetrahydroisoquinolin-2-yl)-1H-pyrrolo[3,2-c]pyridine hydrochloride $^1$H-NMR (CDCl$_3$) δ 8.05 (brs, 1H), 7.22 (brs, 5H), 4.79 (brs, 3H), 4.00 (brs, 2H), 3.22 (brs, 2H), 2.42 (s, 3H), 2.33 (s, 3H), 1.65 (brs, 6H); (Yield: 59.6%)

Example 11

2,3-dimethyl-1-isobutyl-4-(1,2,3,4-tetrahydroisoquinolin-2-yl)-1H-pyrrolo[3,2-c]pyridine hydrochloride $^1$H-NMR (CDCl$_3$) δ 8.08 (m, 1H), 7.22 (brs, 4H), 7.06 (brs, 1H), 4.83 (s, 2H), 4.03 (s, br, 2H), 3.91 (brs, 2H), 3.23 (brs, 2H), 2.38 (s, 3H), 2.34 (s, 3H), 0.96 (brs, 6H); (Yield: 67.6%)

Example 12

2,3-dimethyl-1-(3-methylbutyl)-4-(1,2,3,4-tetrahydroisoquinolin-2-yl)-1H-pyrrolo[3,2-c]pyridine hydrochloride $^1$H-NMR (CDCl$_3$) δ 8.09 (brs, 1H), 7.22 (brs, 4H), 7.04 (brs, 1H), 4.82 (s, 2H), 4.10 (m, 2H), 4.01 (brs, 2H), 3.23 (brs, 2H), 2.38 (s, 3H), 2.33 (s, 3H), 1.71 (m, 1H), 1.61 (m, 2H), 1.02 (d, 6H); (Yield: 66.8%)

Example 13

2,3-dimethyl-1-cyclopropyl-4-(1,2,3,4-tetrahydroisoquinolin-2-yl)-1H-pyrrolo[3,2-c]pyridine hydrochloride $^1$H-NMR (CDCl$_3$) δ 8.33 (brs, 1H), 7.26 (brs, 5H), 4.74 (brs, 2H), 4.22 (brs, 1H), 3.29 (brs, 2H), 2.76 (brs, 2H), 2.31 (brs, 6H), 1.59 (brs, 4H); (Yield: 85.3%)

Example 14

2,3-dimethyl-1-cyclopentyl-4-(1,2,3,4-tetrahydroisoquinolin-2-yl)-1H-pyrrolo[3,2-c]pyridine hydrochloride $^1$H-NMR (CDCl$_3$) δ 8.25 (m, 1H), 7.22 (m, 5H), 4.81 (brs, 2H), 4.64 (brs, 1H), 4.00 (brs, 2H), 3.47 (m, 2H), 2.51 (m, 4H), 2.31 (s, 3+3H), 1.79 (m, 4H); (Yield: 77.5%)

Example 15

2,3-dimethyl-1-cyclopropylmethyl-4-(1,2,3,4-tetrahydroisoquinolin-2-yl)-1H-pyrrolo[3,2-c]pyridine hydrochloride $^1$H-NMR (CDCl$_3$) δ 8.10 (m, 1H), 7.22 (m, 4H), 7.08 (m, 1H), 4.83 (s, 2H), 4.03 (m, 4H), 3.23 (t, 2H), 2.41 (s, 3H), 2.35 (s, 3H), 1.15 (m, 1H), 0.64 (m, 2H), 0.38 (m, 2H); (Yield: 79.6%)

Example 16

1-cyclobutylmethyl-2,3-dimethyl-4-(1,2,3,4-tetrahydroisoquinolin-2-yl)-1H-pyrrolo[3,2-c]pyridine hydrochloride $^1$H-NMR (CDCl$_3$) δ 8.08 (brs, 1H), 7.22 (m, 4H), 7.09 (brs, 1H), 4.82 (s, 2H), 4.12 (d, 2H), 4.02 (t, 2H), 3.22 (t, 2H), 2.72 (m, 1H), 2.38 (s, 3H), 2.33 (s, 3H), 2.05 (m, 2H), 1.89 (m, 2H), 1.78 (m, 2H); (Yield: 66.8%)

Example 17

1-cyclohexylmethyl-2,3-dimethyl-4-(1,2,3,4-tetrahydroisoquinolin-2-yl)-1H-pyrrolo[3,2-c]pyridine hydrochloride $^1$H-NMR (CDCl$_3$) δ 8.07 (s, br, 1H), 7.22 (s, br, 5H), 4.84 (s, br, 2H), 4.10 (m, 4H), 3.23 (s, br, 2H), 2.39 (s, 3H), 2.35 (s, 3H), 1.72 (m, 5H), 1.11 (m, 6H); (Yield: 69.3%)

Example 18

2,3-dimethyl-1-(pent-4-ynyl)-4-(1,2,3,4-tetrahydroisoquinolin-2-yl)-1H-pyrrolo[3,2-c]pyridine hydrochloride $^1$H-NMR (CDCl$_3$) δ 8.09 (brs, 1H), 7.22 (brs, 5H), 4.86 (brs, 2H), 4.13 (m, 4H), 3.24 (brs, 2H), 2.45 (m, 2H), 2.31 (s, 3+3H), 1.88 (m, 1+2H); (Yield: 68.9%)

Example 19

2,3-dimethyl-1-(3-methylbut-2-enyl)-4-(1,2,3,4-tetrahydroisoquinolin-2-yl)-1H-pyrrolo[3,2-c]pyridine hydrochloride $^1$H-NMR (CDCl$_3$) δ 8.07 (brs, 1H), 7.21 (m, 4H), 7.03 (brs, 1H), 5.06 (brs, 1H), 4.81 (s, 2H), 4.70 (brs, 2H), 4.00 (brs, 2H), 3.22 (brs, 2H), 2.36 (s, 3H), 2.33 (s, 3H), 1.86 (s, 3H), 1.75 (s, 3H); (Yield: 53.6%)

Example 20

2,3-dimethyl-1-(2-hydroxyethyl)-4-(1,2,3,4-tetrahydroisoquinolin-2-yl)-1H-pyrrolo[3,2-c]pyridine hydrochloride

$^1$H-NMR (CDCl$_3$) δ 7.78 (brs, 1H), 7.20 (brs, 5H), 4.74 (brs, 2H), 4.57 (brs, 2H), 3.92 (m, 4H), 3.19 (brs, 2H), 2.41 (s, 3H), 2.33 (s, 3H); (Yield: 65.3%)

Example 21

2,3-dimethyl-1-methoxymethyl-4-(1,2,3,4-tetrahydroisoquinolin-2-yl)-1H-pyrrolo[3,2-c]pyridine hydrochloride

$^1$H-NMR (CDCl$_3$) δ 8.14 (brs, 1H), 7.22 (m, 5H), 7.08 (m, 1H), 5.45 (s, 2H), 4.84 (s, 2H), 4.03 (t, 2H), 3.31 (s, 3H), 3.23 (t, 2H), 2.44 (s, 3H), 2.35 (s, 3H); (Yield: 77.5%)

Example 22

2,3-dimethyl-1-(2-ethoxyethyl)-4-(1,2,3,4-tetrahydroisoquinolin-2-yl)-1H-pyrrolo[3,2-c]pyridine hydrochloride

$^1$H-NMR (CDCl$_3$) δ 8.09 (brs, 1H), 7.22 (m, 5H), 4.82 (s, 2H), 4.31 (brs, 2H), 4.02 (brs, 2H), 3.70 (brs, 2H), 3.42 (brs, 2H), 3.23 (brs, 2H), 2.41 (s, 3H), 2.34 (s, 3H), 1.11 (s, 3H); (Yield: 69.5%)

Example 23

2,3-dimethyl-1-(2-methoxyethoxymethyl)-4-(1,2,3,4-tetrahydroisoquinolin-2-yl)-1H-pyrrolo[3,2-c]pyridine hydrochloride

$^1$H-NMR (CDCl$_3$) δ 8.14 (brs, 1H), 7.22 (m, 5H), 5.59 (s, 2H), 4.83 (s, 2H), 4.03 (t, 2H), 3.54 (brs, 4H), 3.38 (s, 3H), 3.23 (t, 2H), 2.44 (s, 3H), 2.34 (s, 3H); (Yield: 58.3%)

Example 24

2,3-dimethyl-1-([1,3]dioxolan-2-ylmethyl)-4-(1,2,3,4-tetrahydroisoquinolin-2-yl)-1H-pyrrolo[3,2-c]pyridine hydrochloride

$^1$H-NMR (CDCl$_3$) δ 8.06 (brs, 1H), 7.22 (brs, 5H), 5.24 (brs, 1H), 4.87 (brs, 2H), 4.15 (brs, 2H), 4.06 (brs, 2H), 3.86 (brs, 2H), 3.72 (brs, 2H), 3.11 (brs, 2H), 2.44 (s, 3H), 2.36 (s, 3H); (Yield: 68.3%)

Example 25

2,3-dimethyl-1-(2-fluorobenzyl)-4-(1,2,3,4-tetrahydroisoquinolin-2-yl)-1H-pyrrolo[3,2-c]pyridine hydrochloride

$^1$H-NMR (CDCl$_3$) δ 8.09 (m, 1H), 7.21 (m, 6H), 7.05 (m, 2H), 6.54 (m, 1H), 5.39 (s, 2H), 4.86 (s, 2H), 4.06 (t, 2H), 3.24 (t, 2H), 2.37 (s, 3H), 2.34 (s, 3H); (Yield: 69.9%)

Example 26

2,3-dimethyl-1-(3-fluorobenzyl)-4-(1,2,3,4-tetrahydroisoquinolin-2-yl)-1H-pyrrolo[3,2-c]pyridine hydrochloride

$^1$H-NMR (CDCl$_3$) δ 8.06 (m, 1H), 7.22 (m, 5H), 7.01 (m, 2H), 6.73 (d, 1H), 6.61 (d, 1H), 5.35 (s, 2H), 4.87 (s, 2H), 4.07 (t, 2H), 3.25 (t, 2H), 2.39 (s, 3H), 2.31 (s, 3H); (Yield: 35.3%)

Example 27

2,3-dimethyl-1-(4-fluorobenzyl)-4-(1,2,3,4-tetrahydroisoquinolin-2-yl)-1H-pyrrolo[3,2-c]pyridine hydrochloride

$^1$H-NMR (CDCl$_3$) δ 8.08 (m, 1H), 7.21 (m, 4H), 7.03 (m, 3H), 6.92 (m, 2H), 5.32 (s, 2H), 4.86 (s, 2H), 4.06 (t, 2H), 3.24 (t, 2H), 2.37 (s, 3H), 2.31 (s, 3H); (Yield: 88.5%)

Example 28

2,3-dimethyl-1-(4-chlorobenzyl)-4-(1,2,3,4-tetrahydroisoquinolin-2-yl)-1H-pyrrolo[3,2-c]pyridine hydrochloride

$^1$H-NMR (CDCl$_3$) δ 8.07 (m, 1H), 7.24 (m, 6H), 7.03 (m, 1H), 6.87 (m, 2H), 5.33 (s, 2H), 4.86 (s, 2H), 4.06 (t, 2H), 3.24 (t, 2H), 2.37 (s, 3H), 2.30 (s, 3H); (Yield: 45.6%)

Example 29

2,3-dimethyl-1-(4-methylbenzyl)-4-(1,2,3,4-tetrahydroisoquinolin-2-yl)-1H-pyrrolo[3,2-c]pyridine hydrochloride

$^1$H-NMR (CDCl$_3$) δ 8.08 (m, 1H), 7.23 (m, 4H), 7.12 (d, 2H), 7.03 (d, 1H), 6.82 (d, 2H), 5.30 (s, 2H), 4.85 (s, 2H), 4.05 (t, 2H), 3.24 (t, 2H), 2.36 (s, 3H), 2.32 (s, 3H), 2.31 (s, 3H); (Yield: 86.5%)

Example 30

2,3-dimethyl-1-(4-methoxybenzyl)-4-(1,2,3,4-tetrahydroisoquinolin-2-yl)-1H-pyrrolo[3,2-c]pyridine hydrochloride

$^1$H-NMR (CDCl$_3$) δ 8.07 (m, 1H), 7.22 (m, 4H), 7.06 (d, 1H), 6.86 (m, 4H), 5.28 (s, 2H), 4.85 (s, 2H), 4.05 (t, 2H), 3.78 (s, 3H), 3.24 (t, 2H), 2.36 (s, 3H), 2.32 (s, 3H); (Yield: 75.9%)

Example 31

2,3-dimethyl-1-(2-methylthiazol-4-ylmethyl)-4-(1,2,3,4-tetrahydroisoquinolin-2-yl)-1H-pyrrolo[3,2-c]pyridine hydrochloride

$^1$H-NMR (CDCl$_3$) δ 8.07 (m, 1H), 7.22 (m, 4H), 7.06 (d, 1H), 6.86 (m, 4H), 5.28 (s, 2H), 4.85 (s, 2H), 4.05 (t, 2H), 3.78 (s, 3H), 3.24 (t, 2H), 2.36 (s, 3H), 2.32 (s, 3H); (Yield: 69.2%)

Example 32

2,3-dimethyl-4-(4-fluorobenzylamino)-1H-pyrrolo[3,2-c]pyridine

A mixture of 4-chloro-2,3-dimethyl-1H-pyrrolo[3,2-c]pyridine (1.16 g, 6.43 mmol) prepared in Preparation 1 and 4-fluorobenzylamine (3 ml, 26.2 mmol) was stirred for 12 hours at 160° C. The reaction mixture was cooled to room temperature and purified with silica gel column chromatography (ethyl acetate: 100%) to give the titled compound as a white solid. (Yield: 83.2%)

$^1$H-NMR (CDCl$_3$/CD$_3$OD) δ 7.33 (brs, 3H), 7.12 (brs, 2H), 6.95 (brs, 1H), 4.76 (brs, 2H), 2.31 (brs, 6H)

Example 33

2,3-dimethyl-4-(4-fluorobenzylamino)-1H-pyrrolo[3,2-c]pyridine hydrochloride 2,3-dimethyl-4-(4-fluorobenzylamino)-1H-pyrrolo[3,2-c]pyridine (1.44 g, 5.34 mmol) prepared in Example 32 was dissolved in ethyl acetate (10 ml). The reaction mixture was saturated with hydrochloric acid gas and then filtered to give the titled compound as a white solid. (Yield: 82.5%)

$^1$H-NMR (CDCl$_3$/CD$_3$OD) δ 7.44 (brs, 3H), 7.06 (brs, 2H), 6.90 (brs, 1H), 4.87 (brs, 2H), 2.33 (brs, 6H)

Example 34

1,2,3-trimethyl-4-(4-fluorobenzylamino)-1H-pyrrolo[3,2-c]pyridine hydrochloride

Sodium hydride (60%, 4.9 mg, 0.118 mmol) was added at room temperature to a solution of 2,3-dimethyl-4-(4-fluorobenzylamino)-1H-pyrrolo[3,2-c]pyridine (20 mg, 0.065 mmol) prepared in Example 32 in N,N-dimethylformamide (1 ml) and then the reaction mixture was stirred for 30 minutes. Iodomethane (7.3 ul, 0.118 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 63.1%).

$^1$H-NMR (CDCl$_3$) δ 7.07-7.94 (m, 6H), 5.78 (brs, 1H), 5.15 (brs, 2H), 3.74 (brs, 3H), 2.37 (brs, 6H)

Examples 35 to 46

The titled compounds of Examples 35 to 46 were prepared, in accordance with the same procedures as in Example 34, using 2,3-dimethyl-4-(4-fluorobenzylamino)-1H-pyrrolo[3,2-c]pyridine prepared in Example 32; and, iodoethane, 1-iodopropane, allyl bromide, 2-bromopropane, 1-bromo-2-methylpropane, (bromomethyl)cyclopropane, 2-bromoethyl methyl ether, 2-bromomethyl-1,3-dioxolane, benzyl bromide, 2-fluorobenzyl bromide, 3-fluorobenzyl bromide, or 4-fluorobenzyl bromide.

Example 35

2,3-dimethyl-1-ethyl-4-(4-fluorobenzylamino)-1H-pyrrolo[3,2-c]pyridine hydrochloride $^1$H-NMR (CDCl$_3$) δ 7.80 (brs, 1H), 7.50 (brs, 2H), 7.07 (brs, 2H), 6.81 (brs, 1H), 5.84 (brs, 1H), 5.13 (brs, 2H), 4.11 (brs, 2H), 2.38 (brs, 3H), 2.34 (brs, 3H), 1.36 (brs, 3H); (Yield: 65.3%)

Example 36

2,3-dimethyl-1-propyl-4-(4-fluorobenzylamino)-1H-pyrrolo[3,2-c]pyridine hydrochloride $^1$H-NMR (CDCl$_3$) δ 7.79 (brs, 1H), 7.50 (brs, 2H), 7.06 (brs, 2H), 6.80 (brs, 1H), 5.86 (brs, 1H), 5.12 (brs, 2H), 4.01 (brs, 2H), 2.38 (brs, 3H), 2.32 (brs, 3H), 1.76 (brs, 2H), 0.96 (brs, 3H); (Yield: 74.5%)

Example 37

1-allyl-2,3-dimethyl-4-(4-fluorobenzylamino)-1H-pyrrolo[3,2-c]pyridine hydrochloride $^1$H-NMR (CDCl$_3$) δ 7.75 (brs, 1H), 7.50 (brs, 2H), 7.06 (brs, 2H), 6.77 (brs, 1H), 5.97 (m, 2H), 5.23 (m, 3H), 4.79 (m, 3H), 2.41 (s, 3H), 2.29 (s, 3H); (Yield: 55.8%)

Example 38

2,3-dimethyl-1-isopropyl-4-(4-fluorobenzylamino)-1H-pyrrolo[3,2-c]pyridine hydrochloride $^1$H-NMR (CDCl$_3$) δ 7.73 (brs, 1H), 7.49 (brs, 2H), 7.06 (brs, 2H), 6.96 (brs, 1H), 5.86 (brs, 1H), 5.12 (brs, 2H), 4.67 (brs, 1H), 2.36 (brs, 6H), 1.61 (brs, 6H); (Yield: 58.9%)

Example 39

1-isobutyl-2,3-dimethyl-4-(4-fluorobenzylamino)-1H-pyrrolo[3,2-c]pyridine hydrochloride $^1$H-NMR (CDCl$_3$) δ 7.73 (brs, 1H), 7.49 (brs, 2H), 7.06 (brs, 2H), 6.96 (brs, 1H), 5.86 (brs, 1H), 5.12 (brs, 2H), 4.67 (brs, 1H), 2.36 (brs, 6H), 1.61 (brs, 6H); (Yield: 75.3%)

Example 40

1-cyclopropylmethyl-2,3-dimethyl-4-(4-fluorobenzylamino)-1H-pyrrolo[3,2-c]pyridine hydrochloride $^1$H-NMR (CDCl$_3$) δ 7.79 (brs, 1H), 7.50 (brs, 2H), 7.07 (brs, 2H), 6.81 (brs, 1H), 5.87 (brs, 1H), 5.12 (brs, 2H), 3.97 (brs, 2H), 2.39 (brs, 3H), 2.35 (brs, 3H), 1.12 (brs, 1H), 0.62 (m, 2H), 0.34 (m, 2H); (Yield: 65.5%)

Example 41

2,3-dimethyl-1-(2-methoxyethyl)-4-(4-fluorobenzylamino)-1H-pyrrolo[3,2-c]pyridine hydrochloride $^1$H-NMR (CDCl$_3$) δ 7.72 (brs, 1H), 7.50 (brs, 2H), 7.03 (brs, 2H), 6.85 (brs, 1H), 6.07 (brs, 1H), 5.10 (brs, 2H), 4.23 (brs, 2H), 3.63 (brs, 2H), 3.27 (brs, 3H), 2.41 (brs, 3H), 2.33 (brs, 3H); (Yield: 67.5%)

Example 42

2,3-dimethyl-1-([1,3]dioxolan-2-ylmethyl)-4-(4-fluorobenzylamino)-1H-pyrrolo[3,2-c]pyridine hydrochloride $^1$H-NMR (CDCl$_3$) δ 7.73 (brs, 1H), 7.56 (brs, 2H), 7.09 (brs, 2H), 6.97 (brs, 1H), 6.07 (brs, 1H), 5.07 (brs, 2H), 4.26 (brs, 2H), 3.71 (m, 4H), 2.38 (brs, 6H); (Yield: 53.6%)

Example 43

1-benzyl-2,3-dimethyl-4-(4-fluorobenzylamino)-1H-pyrrolo[3,2-c]pyridine hydrochloride $^1$H-NMR (CDCl$_3$) δ 6.78-7.73 (m, 11H), 6.07 (brs, 1H), 5.28 (brs, 2H), 5.12 (brs, 2H), 2.42 (brs, 3H), 2.25 (brs, 3H); (Yield: 58.4%)

Example 44

2,3-dimethyl-1-(2-fluorobenzyl)-4-(4-fluorobenzylamino)-1H-pyrrolo[3,2-c]pyridine hydrochloride $^1$H-NMR (CDCl$_3$) δ 7.78 (brs, 1H), 7.52 (brs, 2H), 7.31 (brs, 2H), 7.08 (m, 3H), 6.79 (brs, 1H), 6.53 (brs, 1H), 6.07 (brs, 1H), 5.32 (brs, 2H), 5.15 (brs, 2H), 2.43 (brs, 3H), 2.27 (brs, 3H); (Yield: 35.4%)

Example 45

2,3-dimethyl-1-(3-fluorobenzyl)-4-(4-fluorobenzylamino)-1H-pyrrolo[3,2-c]pyridine hydrochloride $^1$H-NMR (CDCl$_3$) δ 7.78 (brs, 1H), 7.51 (brs, 2H), 7.30 (m, 1H), 7.07 (m, 2H), 7.00 (m, 1H), 6.73 (m, 2H), 6.59 (m, 1H), 5.95 (brs, 1H), 5.28 (brs, 2H), 5.13 (brs, 2H), 2.41 (s, 3H), 2.25 (s, 3H); (Yield: 87.5%)

Example 46

2,3-dimethyl-1-(4-fluorobenzyl)-4-(4-fluorobenzylamino)-1H-pyrrolo[3,2-c]pyridine hydrochloride $^1$H-NMR (CDCl$_3$) δ 7.79 (brs, 1H), 7.51 (brs, 2H), 7.08 (m, 4H), 6.91 (brs, 2H), 6.78 (brs, 1H), 5.93 (brs, 1H), 5.26 (brs, 2H), 5.14 (brs, 2H), 2.41 (brs, 3H), 2.25 (brs, 3H); (Yield: 84.1%)

Example 47

7-[N-benzyl-N-(4-fluorobenzyl)]amino-1,2,3-trimethyl-1H-pyrrolo[3,2-c]pyridine hydrochloride The compound (30 mg, 0.069 mmol) prepared in Example 34 was treated with a saturated sodium bicarbonate solution to obtain 1,2,3-trimethyl-4-(4-fluorobenzylamino)-1H-pyrrolo[3,2-c]pyridine (25 mg, 0.068 mmol). Sodium hydride (60%, 4.2 mg, 0.102 mmol) and benzyl bromide (0.063 ml, 0.086 mmol) were added to a solution of 1,2,3-trimethyl-4-(4-fluorobenzylamino)-1H-pyrrolo[3,2-c]pyridine (25 mg, 0.068 mmol) in N,N-dimethylformamide (2 ml) and then the reaction mixture was stirred for 12 hours at 60° C. The reaction mixture was diluted with ethyl acetate (20 ml) and washed with water (10 ml) three times. The organic layer was separated, dried on anhydrous magnesium sulfate, and then concentrated under reduced pressure. The resulting residue was dissolved in ethyl acetate (1 ml), saturated with hydrochloric acid gas, and then filtered to give the titled compound as a white solid. (Yield: 83.5%).

$^1$H-NMR (CDCl$_3$) δ 8.08 (brs, 1H), 7.30 (m, 3H), 7.21 (m, 4H), 7.10 (m, 1H), 6.99 (m, 2H), 4.70 (s, 4H), 3.76 (s, 3H), 2.47 (s, 3H), 2.41 (s, 3H)

Example 48

7-[N,N-di-(4-fluorobenzyl)]amino-1,2,3-trimethyl-1H-pyrrolo[3,2-c]pyridine hydrochloride In accordance with the same procedures as in Example 47, except for using 1,2,3-trimethyl-4-(4-fluorobenzylamino)-1H-pyrrolo[3,2-c]pyridine obtained by treating the compound of Example 34 with a saturated sodium bicarbonate solution and 4-fluorobenzyl bromide, the titled compound was obtained as a white solid. (Yield: 49.9%)

$^1$H-NMR (CDCl$_3$) δ 8.06 (brs, 1H), 7.19 (brs, 5H), 7.02 (brs, 4H), 4.69 (s, 4H), 3.77 (brs, 3H), 2.47 (s, 3H), 2.42 (s, 3H)

Example 49

7-[N-acetyl-N-(4-fluorobenzyl)]amino-1,2,3-trimethyl-1H-pyrrolo[3,2-c]pyridine hydrochloride The compound (20 mg, 0.061 mmol) prepared in Example 34 was treated with a saturated sodium bicarbonate solution to obtain 1,2,3-trimethyl-4-(4-fluorobenzylamino)-1H-pyrrolo[3,2-c]pyridine (17 mg, 0.060 mmol). Triethylamine (0.013 ml, 0.090 mmol) and acetyl chloride (0.006 ml, 0.090 mmol) were added to a solution of 1,2,3-trimethyl-4-(4-fluorobenzylamino)-1H-pyrrolo[3,2-c]pyridine (17 mg, 0.060 mmol) in tetrahydrofuran (2 nit). The reaction mixture was stirred for 30 minutes at room temperature and concentrated under reduced pressure. The resulting residue was purified with silica gel column chromatography (ethyl acetate), dissolved in ethyl acetate (1 ml), and then saturated with hydrochloric acid gas. The resulting precipitate was filtered to give the titled compound as a white solid. (Yield: 80.5%).

$^1$H-NMR (CDCl$_3$) δ 8.31 (brs, 1H), 7.51 (brs, 1H), 7.21 (m, 2H), 6.84 (t, 2H), 5.53 (d, 1H), 5.08 (d, 1H), 3.82 (s, 3H), 2.39 (s, 3H), 1.88 (s, 3H), 1.85 (s, 3H)

Examples 50 to 53

The titled compounds of Examples 50 to 53 were prepared, in accordance with the same procedures as in Example 49, using isobutyryl chloride, benzoyl chloride, 2-chlorobenzoyl chloride, or phenoxycarbonyl chloride, instead of acetyl chloride.

Example 50

7-[N-isobutyryl-N-(4-fluorobenzyl)]amino-1,2,3-trimethyl-1H-pyrrolo[3,2-c]pyridine hydrochloride $^1$H-NMR (CDCl$_3$) δ 8.33 (brs, 1H), 7.58 (brs, 1H), 7.21 (brs, 2H), 6.84 (brs, 2H), 5.53 (d, 1H), 5.02 (d, 1H), 3.86 (brs, 3H), 2.39 (s, 3H), 2.17 (brs, 1H), 1.81 (s, 3H), 1.14 (s, 3H), 1.04 (s, 3H); (Yield: 53.8%)

Example 51

7-[N-benzoyl-N-(4-fluorobenzyl)]amino-1,2,3-trimethyl-1H-pyrrolo[3,2-c]pyridine hydrochloride $^1$H-NMR (CDCl$_3$) δ 8.28 (brs, 1H), 7.43 (m, 2H), 7.30 (m, 3H), 7.17 (m, 1H), 7.01 (m, 2H), 6.85 (m, 2H), 5.77 (brs, 1H), 5.31 (d, 1H), 3.62 (brs, 3H), 2.19 (s, 3H), 1.79 (s, 3H); (Yield: 45.6%)

Example 52

7-[N-(2-chlorobenzoyl)-N-(4-fluorobenzyl)]amino-1,2,3-trimethyl-1H-pyrrolo[3,2-c]pyridine hydrochloride $^1$H-NMR (CDCl$_3$) δ 8.21 (brs, 1H), 7.46 (m, 5H), 7.11 (m, 2H), 6.76 (m, 2H), 5.30 (brs, 1H), 4.92 (d, 1H), 3.76 (s, 3H), 2.38 (s, 3H), 2.05 (s, 3H); (Yield: 52.3%)

Example 53

7-[N-(4-fluorobenzyl)-N-phenoxycarbonyl]amino-1,2,3-trimethyl-1H-pyrrolo[3,2-c]pyridine hydrochloride $^1$H-NMR (CDCl$_3$) δ 8.29 (brs, 1H), 7.41 (m, 1H), 7.30 (m, 5H), 7.19 (m, 1H), 7.02 (m, 1H), 6.87 (m, 2H), 5.55 (d, 1H), 5.28 (d, 1H), 3.77 (s, 3H), 2.37 (s, 3H), 1.96 (s, 3H); (Yield: 62.3%)

Example 54

3-benzyl-2-methyl-4-(1,2,3,4-tetrahydroisoquinolin-2-yl)-1H-pyrrolo[3,2-c]pyridine In accordance with the same procedures as Example 1, except for using 3-benzyl-4-chloro-2-methyl-1H-pyrrolo[3,2-c]pyridine prepared in Preparation 2 and 1,2,3,4-tetrahydroisoquinoline, the titled compound was obtained as a pale yellow solid. (Yield: 89.7%).

$^1$H-NMR (CDCl$_3$) δ 7.81 (brs, 1H), 7.67 (brs, 1H), 7.02-7.31 (m, 6H), 6.87 (brs, 2H), 6.47 (m, 1H), 4.52 (brs, 2H), 4.22 (brs, 2H), 3.87 (brs, 2H), 2.92 (brs, 2H), 2.39 (s, 3H)

Example 55

3-benzyl-2-methyl-4-(1,2,3,4-tetrahydroisoquinolin-2-yl)-1H-pyrrolo[3,2-c]pyridine hydrochloride In accordance with the same procedures as Example 2, except for using 3-benzyl-2-methyl-4-(1,2,3,4-tetrahydroisoquinolin-2-yl)-1H-pyrrolo[3,2-c]pyridine prepared in Example 54, the titled compound was obtained as a pale yellow solid. (Yield: 89.7%).

$^1$H-NMR (CDCl$_3$) δ 7.82 (brs, 1H), 7.55 (brs, 1H), 7.02-7.26 (m, 6H), 6.90 (brs, 2H), 6.44 (m, 1H), 4.55 (brs, 2H), 4.13 (brs, 2H), 3.84 (brs, 2H), 2.94 (brs, 2H), 2.42 (s, 3H)

Examples 56 to 69

The titled compounds of Examples 56 to 69 were prepared, in accordance with the same procedures as in Example 3, using 3-benzyl-2-methyl-4-(1,2,3,4-tetrahydroisoquinolin-2-yl)-1H-pyrrolo[3,2-c]pyridine prepared in Example 54; and, iodomethane, iodoethane, 1-iodopropane, allyl bromide, 1-bromo-2-methylpropane, bromocyclopropane, (bromomethyl)cyclopropane, 2-bromo ethyl methyl ether, 2-bromoethanol, 2-bromomethyl-1,3-dioxolane, benzyl bromide, 2-fluorobenzyl bromide, 3-fluorobenzyl bromide, or 4-fluorobenzyl bromide.

Example 56

3-benzyl-1,2-dimethyl-4-(1,2,3,4-tetrahydroisoquinolin-2-yl)-1H-pyrrolo[3,2-c]pyridine hydrochloride $^1$H-NMR (CDCl$_3$) δ 8.15 (brs, 1H), 7.00-7.27 (m, 7H), 6.93 (brs, 2H), 6.40 (m, 1H), 4.58 (brs, 2H), 4.16 (brs, 2H), 3.83 (brs, 2H), 3.75 (s, 3H), 2.89 (brs, 2H), 2.32 (s, 3H); (Yield: 58.9%)

Example 57

3-benzyl-1-ethyl-2-methyl-4-(1,2,3,4-tetrahydroisoquinolin-2-yl)-1H-pyrrolo[3,2-c]pyridine hydrochloride $^1$H-NMR (CDCl$_3$) δ 8.16 (brs, 1H), 7.00-7.27 (m, 7H), 6.92 (brs, 2H), 6.38 (m, 1H), 4.58 (brs, 2H), 4.26 (brs, 2H), 4.16 (brs, 2H), 3.94 (brs, 2H), 2.99 (brs, 2H), 2.32 (s, 3H), 1.53 (brs, 3H); (Yield: 98.0%)

Example 58

3-benzyl-1-propyl-2-methyl-4-(1,2,3,4-tetrahydroisoquinolin-2-yl)-1H-pyrrolo[3,2-c]pyridine hydrochloride $^1$H-NMR (CDCl$_3$) δ 8.14 (brs, 1H), 7.00-7.27 (m, 7H), 6.89 (brs, 2H), 6.38 (m, 1H), 4.58 (brs, 2H), 4.16 (brs, 4H), 3.94 (brs, 2H), 2.99 (brs, 2H), 2.31 (s, 3H), 1.86 (brs, 2H), 1.02 (brs, 3H); (Yield: 75.6%)

Example 59

1-allyl-3-benzyl-2-methyl-4-(1,2,3,4-tetrahydroisoquinolin-2-yl)-1H-pyrrolo[3,2-c]pyridine hydrochloride $^1$H-NMR (CDCl$_3$) δ 8.13 (brs, 1H), 6.89-7.26 (m, 9H), 6.38 (d, 1H), 5.94 (m, 1H), 5.28 (d, 1H), 4.83 (m, 3H), 4.59 (brs, 2H), 4.17 (brs, 2H), 3.95 (brs, 2H), 2.99 (brs, 2H), 2.28 (s, 3H); (Yield: 79.1%)

Example 60

3-benzyl-1-isobutyl-2-methyl-4-(1,2,3,4-tetrahydroisoquinolin-2-yl)-1H-pyrrolo[3,2-c]pyridine hydrochloride $^1$H-NMR (CDCl$_3$) δ 8.12 (brs, 1H), 6.90-7.26 (m, 9H), 6.41 (m, 1H), 4.63 (brs, 2H), 4.17 (brs, 2H), 4.00 (brs, 4H), 3.01 (brs, 2H), 2.32 (brs, 3+1H), 1.03 (brs, 6H); (Yield: 80.1%)

Example 61

3-benzyl-1-cyclopropyl-2-methyl-4-(1,2,3,4-tetrahydroisoquinolin-2-yl)-1H-pyrrolo[3,2-c]pyridine hydrochloride $^1$H-NMR (CDCl$_3$) δ 7.82 (brs, 1H), 6.91-7.20 (m, 9H), 6.43 (m, 1H), 4.55 (brs, 2H), 4.12 (brs, 3H), 3.83 (brs, 2H), 2.94 (brs, 2H), 2.41 (s, 3H), 1.70 (brs, 4H); (Yield: 82.5%)

Example 62

3-benzyl-1-cyclopropylmethyl-2-methyl-4-(1,2,3,4-tetrahydroisoquinolin-2-yl)-1H-pyrrolo[3,2-c]pyridine hydrochloride ¹H-NMR (CDCl₃) δ 8.16 (brs, 1H), 6.92-7.24 (m, 9H), 6.39 (m, 1H), 4.59 (brs, 2H), 4.17 (m, 4H), 3.95 (brs, 2H), 2.99 (brs, 2H), 2.33 (s, 3H), 1.24 (m, 1H), 0.69 (brs, 2H), 0.42 (brs, 2H); (Yield: 83.5%)

Example 63

3-benzyl-1-(2-methoxyethyl)-2-methyl-4-(1,2,3,4-tetrahydroisoquinolin-2-yl)-1H-pyrrolo[3,2-c]pyridine hydrochloride ¹H-NMR (CDCl₃) δ 8.13 (brs, 1H), 6.90-7.25 (m, 9H), 6.39 (m, 1H), 4.57 (brs, 2H), 4.36 (brs, 2H), 4.16 (brs, 2H), 3.93 (brs, 2H), 3.71 (brs, 2H), 3.31 (s, 3H), 2.98 (brs, 2H), 2.32 (s, 3H); (Yield: 87.0%)

Example 64

3-benzyl-1-(2-hydroxyethyl)-2-methyl-4-(1,2,3,4-tetrahydroisoquinolin-2-yl)-1H-pyrrolo[3,2-c]pyridine hydrochloride ¹H-NMR (CDCl₃) δ 8.16 (brs, 1H), 6.92-7.33 (m, 9H), 6.37 (m, 1H), 4.58 (brs, 2H), 4.42 (brs, 4H), 4.16 (brs, 2H), 3.51 (brs, 2H), 2.99 (brs, 2H), 2.33 (s, 3H); (Yield: 86.3%)

Example 65

3-benzyl-1-([1,3]dioxolan-2-ylmethyl)-2-methyl-4-(1,2,3,4-tetrahydroisoquinolin-2-yl)-1H-pyrrolo[3,2-c]pyridine hydrochloride ¹H-NMR (CDCl₃) δ 8.12 (brs, 1H), 6.88-7.22 (m, 9H), 6.43 (m, 1H), 5.26 (brs, 1H), 4.58 (brs, 2H), 4.39 (brs, 2H), 4.16 (brs, 2H), 3.93 (brs, 2H), 3.85 (brs, 2H), 3.68 (brs, 2H), 2.98 (brs, 2H), 2.45 (s, 3H); (Yield: 74.9%)

Example 66

1,3-dibenzyl-2-methyl-4-(1,2,3,4-tetrahydroisoquinolin-2-yl)-1H-pyrrolo[3,2-c]pyridine hydrochloride ¹H-NMR (CDCl₃) δ 8.13 (brs, 1H), 6.92-7.36 (m, 14H), 6.40 (m, 1H), 5.42 (brs, 2H), 4.62 (brs, 2H), 4.19 (brs, 2H), 3.97 (brs, 2H), 3.00 (brs, 2H), 2.34 (s, 3H); (Yield: 85.3%)

Example 67

3-benzyl-1-(2-fluorobenzyl)-2-methyl-4-(1,2,3,4-tetrahydroisoquinolin-2-yl)-1H-pyrrolo[3,2-c]pyridine hydrochloride ¹H-NMR (CDCl₃) δ 8.12 (brs, 1H), 6.92-7.35 (m, 12H), 6.61 (brs, 1H), 6.40 (m, 1H), 5.46 (brs, 2H), 4.62 (brs, 2H), 4.19 (brs, 2H), 3.98 (brs, 2H), 3.01 (brs, 2H), 2.27 (s, 3H); (Yield: 78.6%)

Example 68

3-benzyl-1-(3-fluorobenzyl)-2-methyl-4-(1,2,3,4-tetrahydroisoquinolin-2-yl)-1H-pyrrolo[3,2-c]pyridine hydrochloride ¹H-NMR (CDCl₃) δ 8.13 (brs, H), 7.34 (brs, 2H), 7.15 (m, 4H), 7.03 (brs, 3H), 6.85 (brs, 2H), 6.76 (brs, 1H), 6.66 (brs, 1H), 6.42 (brs, 1H), 5.42 (brs, 2H), 4.64 (brs, 2H), 4.20 (brs, 2H), 4.00 (brs, 2H), 3.02 (brs, 2H), 2.25 (s, 3H); (Yield: 81.1%)

Example 69

3-benzyl-1-(4-fluorobenzyl)-2-methyl-4-(1,2,3,4-tetrahydroisoquinolin-2-yl)-1H-pyrrolo[3,2-c]pyridine hydrochloride ¹H-NMR (CDCl₃) δ 8.13 (brs, 1H), 6.91-7.24 (m, 13H), 6.39 (m, 1H), 5.40 (brs, 2H), 4.62 (brs, 2H), 4.19 (brs, 2H), 3.98 (brs, 2H), 3.01 (brs, 2H), 2.23 (s, 3H); (Yield: 88.8%)

Example 70

3-benzyl-2-methyl-4-(1,2,3,4-tetrahydroisoquinolin-2-yl)-1H-pyrrolo[3,2-c]pyridine sodium Sodium hydride (4.56 mg, 0.19 mmol) was added to a solution of 3-benzyl-2-methyl-4-(1,2,3,4-tetrahydroisoquinolin-2-yl)-1H-pyrrolo[3,2-c]pyridine (70 mg, 0.19 mmol) prepared in Example 54 in anhydrous tetrahydrofuran (3 ml) and then the reaction mixture was stirred for 1 hour at room temperature. The reaction mixture was concentrated under reduced pressure and recrystallized to give the titled compound as a white solid. (Yield: 75.2%)

¹H-NMR (CDCl₃) δ 7.82 (brs, 1H), 7.55 (brs, 1H), 7.02-7.26 (m, 6H), 6.90 (brs, 2H), 6.44 (m, 1H), 4.55 (brs, 2H), 4.13 (brs, 2H), 3.84 (brs, 2H), 2.94 (brs, 2H), 2.42 (s, 3H)

Example 71

3-benzyl-2-methyl-4-(4-fluorobenzylamino)-1H-pyrrolo[3,2-c]pyridine hydrochloride Cesium carbonate (85 mg, 0.26 mmol), (S)-2,2'-bis(diphenylphosphino)-1,1'-binaphthalene (11 mg, 0.020 mmol), tris(dibenzylideneacetone)dipalladium(0) (8 mg, 0.009 mmol), and 4-fluorobenzylamine (0.035 ml, 0.26 mmol) were added to a solution of 3-benzyl-4-chloro-2-methyl-1H-pyrrolo[3,2-c]pyridine (50 mg, 0.17 mmol) prepared in Preparation 2 in toluene (3 ml). The reaction mixture was refluxed under stirring for 2 days. The reaction mixture was cooled to room temperature, filtered, and then concentrated under reduced pressure. The resulting residue was purified with silica gel column chromatography, dissolved in ethyl ether (2 ml), and then saturated with hydrochloric acid gas. The resulting precipitate was filtered to give the titled compound as a white solid. (Yield: 35.2%)

¹H-NMR (CDCl₃) δ 7.62 (m, 2H), 7.44 (m, 3H), 7.25 (m, 6H), 4.92 (d, 2H), 4.54 (s, 2H), 2.57 (s, 3H)

Example 72

3-benzyl-1,2-dimethyl-4-(4-fluorobenzylamino)-1H-pyrrolo[3,2-c]pyridine hydrochloride The compound (25 mg, 0.066 mmol) prepared in Example 71 was treated with a saturated sodium bicarbonate solution to obtain 3-benzyl-2-methyl-4-(4-fluorobenzylamino)-1H-pyrrolo[3,2-c]pyridine (22 mg, 0.065 mmol). Sodium hydride (60%, 4.9 mg, 0.118 mmol) was added at room temperature to a solution of 3-benzyl-2-methyl-4-(4-fluorobenzylamino)-1H-pyrrolo[3,2-c]pyridine (22 mg, 0.065 mmol) in N,N-dimethylformamide (1 ml) and then the reaction mixture was stirred for 30 minutes. Iodomethane (0.007 ml, 0.118 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 52.1%)

$^1$H-NMR (CDCl$_3$) δ 7.77 (m, 2H), 7.32 (m, 3H), 7.28 (m, 6H), 4.96 (d, 2H), 4.47 (s, 2H), 3.43 (brs, 3H), 2.57 (s, 3H)

Example 73

3-benzyl-2-methyl-4-(4-chlorobenzylamino)-1H-pyrrolo[3,2-c]pyridine hydrochloride Cesium carbonate (85 mg, 0.26 mmol), (S)-2,2'-bis(diphenylphosphino)-1,1'-binaphthalene (11 mg, 0.020 mmol), tris(dibenzylideneacetone)dipalladium(0) (8 mg, 0.009 mmol), and 4-chlorobenzylamine (0.032 ml, 0.26 mmol) were added to a solution of 3-benzyl-4-chloro-2-methyl-1H-pyrrolo[3,2-c]pyridine (50 mg, 0.17 mmol) prepared in Preparation 2 in toluene (3 ml). The reaction mixture was refluxed under stirring for 2 days. The reaction mixture was cooled to room temperature, filtered, and then concentrated under reduced pressure. The resulting residue was purified with silica gel column chromatography, dissolved in ethyl ether (2 ml), and then saturated with hydrochloric acid gas. The resulting precipitate was filtered to give the titled compound as a white solid. (Yield: 42.2%)

$^1$H-NMR (CDCl$_3$) δ 7.64 (m, 2H), 7.36 (m, 3H), 7.22 (m, 6H), 4.95 (d, 2H), 4.49 (s, 2H), 2.52 (s, 3H)

Example 74

3-benzyl-1,2-dimethyl-4-(4-chlorobenzylamino)-1H-pyrrolo[3,2-c]pyridine hydrochloride The compound (30 mg, 0.12 mmol) prepared in Example 73 was treated with a saturated sodium bicarbonate solution to obtain 3-benzyl-2-methyl-4-(4-chlorobenzylamino)-1H-pyrrolo[3,2-c]pyridine (24 mg, 0.065 mmol). Sodium hydride (60%, 4.9 mg, 0.118 mmol) was added at room temperature to a solution of 3-benzyl-2-methyl-4-(4-chlorobenzylamino)-1H-pyrrolo[3,2-c]pyridine (24 mg, 0.065 mmol) in N,N-dimethylformamide (1 ml) and then the reaction mixture was stirred for 30 minutes. Iodomethane (0.007 ml, 0.118 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 58.2%)

$^1$H-NMR (CDCl$_3$) δ 7.87 (m, 2H), 7.34 (m, 3H), 7.23 (m, 6H), 4.86 (d, 2H), 4.36 (s, 2H), 3.47 (brs, 3H), 2.54 (s, 3H)

Example 75

3-benzyl-2-methyl-4-(4-fluorobenzyloxy)-1H-pyrrolo[3,2-c]pyridine hydrochloride

Cesium carbonate (93 mg, 0.28 mmol), (S)-2,2'-bis(diphenylphosphino)-1,1'-binaphthalene (12 mg, 0.021 mmol), tris(dibenzylideneacetone)dipalladium(0) (9 mg, 0.010 mmol), and 4-fluorobenzyl alcohol (0.031 ml, 0.28 mmol) were added to a solution of 3-benzyl-4-chloro-2-methyl-1H-pyrrolo[3,2-c]pyridine (50 mg, 0.17 mmol) prepared in Preparation 2 in toluene (3 ml). The reaction mixture was refluxed under stirring for 2 days. The reaction mixture was cooled to room temperature, filtered, and then concentrated under reduced pressure. The resulting residue was purified with silica gel column chromatography and then recrystallized in n-hexane (5 ml). The resulting solid was dissolved in ethyl ether (2 ml), saturated with hydrochloric acid gas, and then filtered to give the titled compound as a white solid. (Yield: 42.3%)

$^1$H-NMR (CDCl$_3$) δ 7.65 (bs, 1H), 7.33 (m, 3H), 7.16 (m, 4H), 6.97 (m, 2H), 6.87 (m, 1H), 5.72 (s, 2H), 4.06 (s, 2H), 2.49 (s, 3H)

Example 76

3-benzyl-1,2-dimethyl-4-(4-fluorobenzyloxy)-1H-pyrrolo[3,2-c]pyridine hydrochloride The compound (27 mg, 0.066 mmol) prepared in Example 75 was treated with a saturated sodium bicarbonate solution to obtain 3-benzyl-2-methyl-4-(4-fluorobenzyloxy)-1H-pyrrolo[3,2-c]pyridine (23 mg, 0.065 mmol). Sodium hydride (60%, 4.9 mg, 0.118 mmol) was added at room temperature to a solution of 3-benzyl-2-methyl-4-(4-fluorobenzyloxy)-1H-pyrrolo[3,2-c]pyridine (23 mg, 0.065 mmol) in N,N-dimethylformamide (1 ml) and then the reaction mixture was stirred for 30 minutes. Iodomethane (0.007 ml, 0.118 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 59.3%)

$^1$H-NMR (CDCl$_3$) δ 7.62 (brs, 1H), 7.31 (m, 3H), 7.12 (m, 4H), 6.88 (m, 2H), 6.85 (m, 1H), 5.71 (s, 2H), 4.08 (s, 2H), 3.43 (brs, 3H), 2.45 (s, 3H)

Example 77

3-benzyl-2-methyl-4-(4-chlorobenzyloxy)-1H-pyrrolo[3,2-c]pyridine hydrochloride

Cesium carbonate (93 mg, 0.28 mmol), (S)-2,2'-bis(diphenylphosphino)-1,1'-binaphthalene (12 mg, 0.021 mmol), tris(dibenzylideneacetone)dipalladium(0) (9 mg, 0.010 mmol), and 4-chlorobenzyl alcohol (0.039 ml, 0.28 mmol) were added to a solution of 3-benzyl-4-chloro-2-methyl-1H-pyrrolo[3,2-c]pyridine (50 mg, 0.17 mmol) prepared in Preparation 2 in toluene (3 ml). The reaction mixture was refluxed under stirring for 2 days. The reaction mixture was cooled to room temperature, filtered, and then concentrated under reduced pressure. The resulting residue was purified with silica gel column chromatography and then recrystallized in n-hexane (3 ml). The resulting solid was dissolved in ethyl ether (2 ml), saturated with hydrochloric acid gas, and then filtered to give the titled compound as a white solid. (Yield: 41.2%)

$^1$H-NMR (CDCl$_3$) δ 7.68 (brs, 1H), 7.22 (m, 3H), 7.11 (m, 4H), 6.99 (m, 2H), 6.75 (m, 1H), 5.72 (s, 2H), 4.02 (s, 2H), 2.42 (s, 3H)

Example 78

3-benzyl-1,2-dimethyl-4-(4-chlorobenzyloxy)-1H-pyrrolo[3,2-c]pyridine hydrochloride The compound (30 mg, 0.066 mmol) prepared in Example 77 was treated with a saturated sodium bicarbonate solution to obtain 3-benzyl-2-methyl-4-(4-chlorobenzyloxy)-1H-pyrrolo[3,2-c]pyridine (24 mg, 0.065 mmol). Sodium hydride (60%, 4.9 mg, 0.118 mmol) was added at room temperature to a solution of 3-benzyl-2-methyl-4-(4-chlorobenzyloxy)-1H-pyrrolo[3,2-c]pyridine (24 mg, 0.065 mmol) in N,N-dimethylformamide (1 ml) and then the reaction mixture was stirred for 30 minutes. Iodomethane (0.007 ml, 0.118 mmol) was added to the reaction mixture, which was then stirred for 1 hour at room temperature. The reaction mixture was diluted with ethyl acetate (10 ml) and washed with water (10 ml) three times. The organic layer was separated, dried on anhydrous magnesium sulfate, and then concentrated. The resulting residue was dissolved in ethyl acetate (1 ml), saturated with hydrochloric acid gas, and then filtered to give the titled compound as a white solid. (Yield: 57.1%)

$^1$H-NMR (CDCl$_3$) δ 7.61 (brs, 1H), 7.33 (m, 3H), 7.19 (m, 4H), 6.82 (m, 2H), 6.77 (m, 1H), 5.65 (s, 2H), 4.01 (s, 2H), 3.41 (brs, 3H), 2.46 (s, 3H)

Example 79

3-(3-fluorobenzyl)-2-methyl-4-(1,2,3,4-tetrahydroisoquinolin-2-yl)-1H-pyrrolo[3,2-c]pyridine hydrochloride In accordance with the same procedures as Examples 1 and 2, except for using 4-chloro-3-(fluorobenzyl)-2-methyl-1H-pyrrolo[3,2-c]pyridine prepared in Preparation 3 and 1,2,3,4-tetrahydroisoquinoline, the titled compound was obtained as a pale yellow solid. (Yield: 88.5%)

$^1$H-NMR (CDCl$_3$) δ 7.81 (brs, 1H), 7.52 (brs, 1H), 7.26 (m, 3H), 7.10 (s, 1H), 6.90 (brs, 2H), 6.41 (m, 1H), 4.52 (brs, 2H), 4.22 (brs, 2H), 3.65 (brs, 2H), 2.89 (brs, 2H), 2.41 (s, 3H)

Example 80

3-(3-fluorobenzyl)-1,2-dimethyl-4-(1,2,3,4-tetrahydroisoquinolin-2-yl)-1H-pyrrolo[3,2-c]pyridine hydrochloride The compound (25 mg, 0.055 mmol) prepared in Example 79 was treated with a saturated sodium bicarbonate solution to obtain 3-(3-fluorobenzyl)-2-methyl-4-(1,2,3,4-tetrahydroisoquinolin-2-yl)-1H-pyrrolo[3,2-c]pyridine (17 mg, 0.054 mmol). Sodium hydride (60%, 4.3 mg, 0.108 mmol) was added at room temperature to a solution of 3-(3-fluorobenzyl)-2-methyl-4-(1,2,3,4-tetrahydroisoquinolin-2-yl)-1H-pyrrolo[3,2-c]pyridine (17 mg, 0.054 mmol) in N,N-dimethylformamide (1 ml) and then the reaction mixture was stirred for 30 minutes. Iodomethane (0.004 ml, 0.06 mmol) was added to the reaction mixture, which was then stirred for 1 hour at room temperature. The reaction mixture was diluted with ethyl acetate (10 ml) and washed with water (10 ml) three times. The separated organic layer was dried on anhydrous magnesium sulfate, and then concentrated. The resulting residue was dissolved in ethyl acetate (1 ml), saturated with hydrochloric acid gas, and then filtered to give the titled compound as a white solid. (Yield: 51.2%)

$^1$H-NMR (CDCl$_3$) δ 8.13 (m, 1H), 7.20 (m, 2H), 7.11 (m, 1H), 7.07 (m, 1H), 4.77 (s, 2H), 3.97 (m, 2H), 3.72 (s, 3H), 3.21 (m, 2H), 2.41 (s, 3H), 2.32 (s, 3H)

Example 81

3-allyl-2-methyl-4-(1,2,3,4-tetrahydroisoquinolin-2-yl)-1H-pyrrolo[3,2-c]pyridine hydrochloride In accordance with the same procedures as Examples 1 and 2, except for using 3-allyl-4-chloro-2-methyl-1H-pyrrolo[3,2-c]pyridine prepared in Preparation 4 and 1,2,3,4-tetrahydroisoquinoline, the titled compound was obtained as a pale yellow solid. (Yield: 77.4%)

$^1$H-NMR (CDCl$_3$) δ 6.45 (d, 1H), 6.10 (d, 1H), 5.66 (m, 1H), 4.71 (d, 1H), 4.63 (d, 1H), 4.22 (brs, 2H), 3.65 (brs, 2H), 3.22 (d, 2H), 2.89 (brs, 2H), 1.95 (s, 3H)

Example 82

3-allyl-1,2-dimethyl-4-(1,2,3,4-tetrahydroisoquinolin-2-yl)-1H-pyrrolo[3,2-c]pyridine hydrochloride The compound (20 mg, 0.056 mmol) prepared in Example 81 was treated with a saturated sodium bicarbonate solution to obtain 3-allyl-2-methyl-4-(1,2,3,4-tetrahydroisoquinolin-2-yl)-1H-pyrrolo[3,2-c]pyridine (14 mg, 0.054 mmol). Sodium hydride (60%, 4.3 mg, 0.108 mmol) was added at room temperature to a solution of 3-allyl-2-methyl-4-(1,2,3,4-tetrahydroisoquinolin-2-yl)-1H-pyrrolo[3,2-c]pyridine (14 mg, 0.054 mmol) in N,N-dimethylformamide (1 ml) and then the reaction mixture was stirred for 30 minutes. Iodomethane (0.004 ml, 0.06 mmol) was added to the reaction mixture, which was then stirred for 1 hour at room temperature. The reaction mixture was diluted with ethyl acetate (10 ml) and washed with water (10 ml) three times. The organic layer was separated, dried on anhydrous magnesium sulfate, and then concentrated. The resulting residue was dissolved in ethyl acetate (1 ml), saturated with hydrochloric acid gas, and then filtered to give the titled compound as a white solid. (Yield: 42.3%)

$^1$H-NMR (CDCl$_3$) δ 6.45 (d, 1H), 6.10 (d, 1H), 5.66 (m, 1H), 4.71 (d, 1H), 4.63 (d, 1H), 4.22 (brs, 2H), 3.65 (brs, 2H), 3.22 (d, 2H), 2.89 (brs, 2H), 2.55 (s, 3H), 1.95 (s, 3H)

Test Example 1

Inhibitory Effects on Proton Pump (H$^+$/K$^+$-ATPase) Activity 1-1. Preparation of Gastric Proton Pump Vesicles The hog fundic regions containing parietal and peptic cells were scraped with slide-glass. The collected cells were suspended in 10 ml of 0.25M sucrose buffer and homogenized using a tight-fitting Teflon-glass homogenizer. The homogenate was centrifuged for 35 min at 8,000 rpm and the pellet was discarded. The supernatant was further centrifuged for 75 min at 25,000 rpm. The resulting pellets were re-suspended in the sucrose buffer (10 ml), and then the suspension was laid onto discontinuous density gradients consisting of 0.25M sucrose buffer and isolation medium containing 9% Ficoll (w/w). After being centrifuged for 3 hours and 15 minutes at 100,000×g, the material at the interface of sucrose buffer and Ficoll solution was collected and then centrifuged for 40 minutes at 100,000×g. The resulting pellets were re-suspended in 1 ml of 5 mM Hepes/Tris buffer (pH 6.1). This material was lyophilized and stored at −70° C. and used as an enzyme source of the in vitro enzyme reaction assay of proton pump.

1-2. Measurement of Inhibitory Effects on Proton Pump (H+/K+-ATPase) Activity

The inhibitory effects of the compounds of the present invention against proton pump activity were evaluated in 96-well plate. In this assay, the $K^+$ specific $H^+/K^+$-ATPase activity was calculated based on the difference between the activity of $H^+/K^+$-ATPase activity with $K^+$ and without $K^+$ ion. In 96-well plate, 1% dimethylsulfoxide (DMSO) in buffer was added to negative and positive control groups and the diluted compounds of the present invention in buffer were added to test group. All assays were performed in 100 μl reaction volume at room temperature, and the hog gastric vesicle was kept in ice before use. At the beginning of the reaction, 10 μl of reaction buffer containing 1% DMSO was added to the negative and positive control groups and to each concentration of compounds in the test group. Then lyophilized vesicle in 5 mM Pipes/Tris buffer (pH 6.1) was pre-incubated in the presence of various concentrations of test compounds. After a 5 minute incubation, negative and positive buffers were respectively added to the previous reaction mixture. As the substrate, ATP was added to the reaction buffer, and incubated for 30 minutes at 37° C. Enzymatic activity was stopped by the addition of colorimetric reagent (2× malachite green, 1× ammonium molybdate, 1× polyvinyl alcohol, 2× $H_2O$) and the amount of mono phosphate (Pi) in the reaction was measured at 620 nm using the micro plate reader (Genios Pro, TECAN). The difference between the Pi production with $K^+$ and without $K^+$ is taken as $K^+$ stimulated $H^+/K^+$-ATPase activity. The $IC_{50}$s of test compounds were calculated from each % inhibition value of compounds using the method of Litchfield-Wilcoxon (*J. Pharmacol. Exp. Ther.* (1949) 96, 99). The results are shown in Table 1.

TABLE 1

| Example | $IC_{50}$ (uM) |
|---|---|
| 1 | 0.47 |
| 2 | 0.47 |
| 3 | 2.05 |
| 6 | 0.43 |
| 7 | 1.03 |
| 20 | <4.0 |
| 55 | 0.09 |
| 56 | 0.23 |
| 61 | 0.28 |
| 63 | <4.0 |
| 65 | 2.12 |
| 66 | <4.0 |
| 70 | 0.22 |
| 71 | 0.53 |

As shown in Table 1, the compounds of the present invention have excellent inhibitory effects on gastric $H^+/K^+$-ATPase.

Test Example 2

Inhibitory Effects on Basal Gastric Acid Secretion in Pylorus-Ligated Rats

Inhibitory effects of the compounds of the present invention on basal gastric acid secretion were performed according to Shay's rat model (Shay, H., et al., 1945, gastroenterology, 5, 43-61). Male Sprague Dawley (SD) rats (200±10 g body weight) were divided into 3 groups (n=5) and fasted for 24 hours with free access to water. Control group was orally administered with 0.5% methylcellulose alone and the other groups were orally administered with test compounds suspended in 0.5% methylcellulose solution at doses of 1, 3 and 10 mg/kg/5 ml one hour before pylorus ligation.

Under ether anesthesia, the abdomens of the rats were incised and then the pylorus was ligated. 5 hours after ligation, the animals were sacrificed, and the gastric contents were collected. The collected contents were centrifuged at 1,000×g for 10 minutes to obtain the gastric juice. Total acid output was measured by 0.01 N NaOH volume (ueq/ml) for automatic titration of the gastric juice to pH 7.0 and the $ED_{50}$s of test compounds were calculated using the Litchfield-Wilcoxon method. % inhibitory activity was calculated from the following equation and the results are shown in Table 2.

% inhibitory activity of test compound=(total acid output of control group−total acid output of the group treated with test compounds)/total acid output of control group×100

TABLE 2

| Example | $ED_{50}$ (mg/kg) |
|---|---|
| 55 | 1.6 |
| 56 | 2.9 |

As shown in Table 2, the compounds of the present invention have potent inhibition activities against basal gastric acid secretion in pylorus-ligated rats.

Test Example 3

Reversible Inhibition of Hog Gastric $H^+/K^+$-ATPase 3-1. Preparation of gastric vesicles Gastric vesicles were prepared from hog fundic mucosa using the method of Saccomani et al. (Saccomani G, Stewart H B, Shqw D, Lewin M and Sachs G, Characterization of gastric mucosal membranes. IX. Fraction and purification of K-ATPase-containing vesicles by zonal centrifugation and free-flow electrophoresis technique. *Biochem. Biophy. Acta.* (BBA)-Biomembranes 465, 311-330, 1977). This material was lyophilized and stored at −70° C. The protein content of gastric vesicles was determined by the Bradford method using bovine serum albumin as a standard (Bradford MM, A rapid and sensitive method for the quantitation of microgram quantities of protein utilizing the principle of protein-dye binding. *Anal Biochem.* 72, 248-254, 1976).

3-2. Determination of Reversible Inhibition of Hog Gastric $H^+/K^+$-ATPase

Activity of $H^+/K^+$-ATPase in hog microsome (lyophilized vesicle) was measured by the inorganic phosphate released from ATP using an one-step colorimetric detection method at the concentration at which the test compounds have 50% inhibition of the proton pump (Chan K M, Delfert D, and Junger K D, A direct colorimetric assay for $Ca^{2+}$-stimulated ATPase activity. *Anal Biochem*, 157, 375-380, 1986). The mode of action of test compounds on $H^+/K^+$-ATPase was investigated according to the Washout method (Beil W, Staar U, and Sewing K F, Substituted thieno[3,4-d]imidazoles, a novel group of $H^+/K^+$-ATPase inhibitors. Differentiation of their inhibition characteristics from those of omeprazole. *Eur. J. Pharmacol.*, 187, 455-67, 1990).

Lyophilized vesicle in the solution of 5 mM Pipes/Tris buffer was pre-incubated in the presence of the test compound (the compound of Example 55) at the concentration at which it has 50% inhibition of the proton pump. The previous reaction buffer was added with 2 mM MgCl$_2$, 50 mM KCl, 5 uM Valinomycin, and 0.5 mM ATP and then incubated for 30 minutes at 37° C. The H$^+$/K$^+$-ATPase activity was measured using the colorimetric detection method and then the test sample was centrifuged at 100,000×g for 1 hr. The vesicles are present in the form of pellets in the test sample. The supernatant thereof was replaced with the same buffer not having the test compound. The test sample was pre-incubated for 5 minutes at room temperature and then incubated further for 30 minutes at 37° C. The H$^+$/K$^+$-ATPase activity was also measured using the colorimetric detection method. The H$^+$/K$^+$-ATPase activity before washout and after washout in the test sample was analyzed, in comparison with those in the non-treated group.

As a result, the compound of Example 55 inhibited H$^+$/K$^+$-ATPase activity by 50% before washout and did not inhibit H$^+$/K$^+$-ATPase activity after washout; the gastric H$^+$/K$^+$-ATPase activity by the compound of Example 55 was completely recovered to non-treated group level after washout. These results confirm that the compounds of formula (I) exhibited reversible inhibition of the gastric H$^+$/K$^+$-ATPase.

What is claimed is:

1. A compound of the formula (I) or a pharmaceutically acceptable salt thereof:

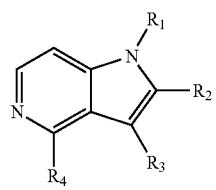

(I)

wherein:
  R$_1$ is hydrogen; a straight or branched C$_1$-C$_6$ alkyl group, optionally substituted with one or more substituents selected from the group consisting of C$_1$-C$_5$ alkoxy, hydroxy, C$_3$-C$_7$ cycloalkyl, C$_1$-C$_3$ alkyl-thiazolyl, and 1,3-dioxolanyl; a straight or branched C$_2$-C$_6$ alkenyl group; a straight or branched C$_2$-C$_6$ alkynyl group; a C$_3$-C$_7$ cycloalkyl group; or a benzyl group, optionally substituted with one or more substituents selected from the group consisting of halogen, C$_1$-C$_3$ alkyl, and C$_1$-C$_3$ alkoxy,
  R$_2$ is a straight or branched C$_1$-C$_6$ alkyl group,
  R$_3$ is hydrogen; a straight or branched C$_1$-C$_6$ alkyl group; a straight or branched C$_2$-C$_6$ alkenyl group; or a benzyl group optionally one or more substituted with halogen, and
  R$_4$ is an amino group substituted with one or two substituents selected from the group consisting of hydrogen, straight or branched C$_1$-C$_5$ alkylcarbonyl, phenoxycarbonyl, benzyl optionally one or more substituted with halogen, and benzoyl optionally one or more substituted with halogen.

2. The compound or a pharmaceutically acceptable salt thereof according to claim 1, wherein R$_1$ is hydrogen; a straight or branched C$_1$-C$_6$ alkyl group; a C$_1$-C$_3$ alkyl group substituted with one or more substituents selected from the group consisting of methoxy, ethoxy, hydroxy, cyclopropyl, cyclobutyl, cyclohexyl, methylthiazolyl, and 1,3-dioxolanyl; a straight or branched C$_2$-C$_6$ alkenyl group; a straight or branched C$_2$-C$_6$ alkynyl group; cyclopropyl; cyclopentyl; or a benzyl group, optionally substituted with one or more substituents selected from the group consisting of halogen, methyl, and methoxy,
  R$_2$ is a straight or branched C$_1$-C$_3$ alkyl group,
  R$_3$ is hydrogen; a straight or branched C$_1$-C$_3$ alkyl group; a straight or branched C$_2$-C$_5$ alkenyl group; or a benzyl group optionally one or more substituted with halogen, and
  R$_4$ is an amino group substituted with one or two substituents selected from the group consisting of hydrogen, straight or branched C$_1$-C$_5$ alkylcarbonyl, phenoxycarbonyl, benzyl optionally one or more substituted with halogen, and benzoyl optionally one or more substituted with halogen.

3. The compound or a pharmaceutically acceptable salt thereof according to claim 1, which is selected from the group consisting of:
  2,3-dimethyl-4-(4-fluorobenzylamino)-1H-pyrrolo[3,2-c]pyridine,
  2,3-dimethyl-4-(4-fluorobenzylamino)-1H-pyrrolo[3,2-c]pyridine hydrochloride;
  1,2,3-trimethyl-4-(4-fluorobenzylamino)-1H-pyrrolo[3,2-c]pyridine hydrochloride;
  2,3-dimethyl-1-ethyl-4-(4-fluorobenzylamino)-1H-pyrrolo[3,2-c]pyridine hydrochloride;
  2,3-dimethyl-1-propyl-4-(4-fluorobenzylamino)-1H-pyrrolo[3,2-c]pyridine hydrochloride;
  1-allyl-2,3-dimethyl-4-(4-fluorobenzylamino)-1H-pyrrolo[3,2-c]pyridine hydrochloride;
  2,3-dimethyl-1-isopropyl-4-(4-fluorobenzylamino)-1H-pyrrolo[3,2-c]pyridine hydrochloride;
  1-isobutyl-2,3-dimethyl-4-(4-fluorobenzylamino)-1H-pyrrolo[3,2-c]pyridine hydrochloride;
  1-cyclopropylmethyl-2,3-dimethyl-4-(4-fluorobenzylamino)-1H-pyrrolo[3,2-c]pyridine hydrochloride;
  2,3-dimethyl-1-(2-methoxyethyl)-4-(4-fluorobenzylamino)-1H-pyrrolo[3,2-c]pyridine hydrochloride;
  2,3-dimethyl-1-([1,3]dioxolan-2-ylmethyl)-4-(4-fluorobenzylamino)-1H-pyrrolo[3,2-c]pyridine hydrochloride;
  1-benzyl-2,3-dimethyl-4-(4-fluorobenzylamino)-1H-pyrrolo[3,2-c]pyridine hydrochloride;
  2,3-dimethyl-1-(2-fluorobenzyl)-4-(4-fluorobenzylamino)-1H-pyrrolo[3,2-c]pyridine hydrochloride;
  2,3-dimethyl-1-(3-fluorobenzyl)-4-(4-fluorobenzylamino)-1H-pyrrolo[3,2-c]pyridine hydrochloride;
  2,3-dimethyl-1-(4-fluorobenzyl)-4-(4-fluorobenzylamino)-1H-pyrrolo[3,2-c]pyridine hydrochloride;
  7-[N-benzyl-N-(4-fluorobenzyl)]amino-1,2,3-trimethyl-1H-pyrrolo[3,2-c]pyridine hydrochloride;
  7-[N,N-di-(4-fluorobenzyl)]amino-1,2,3-trimethyl-1H-pyrrolo[3,2-c]pyridine hydrochloride;
  7-[N-acetyl-N-(4-fluorobenzyl)]amino-1,2,3-trimethyl-1H-pyrrolo[3,2-c]pyridine hydrochloride;
  7-[N-isobutyryl-N-(4-fluorobenzyl)]amino-1,2,3-trimethyl-1H-pyrrolo[3,2-c]pyridine hydrochloride;
  7-[N-benzoyl-N-(4-fluorobenzyl)]amino-1,2,3-trimethyl-1H-pyrrolo[3,2-c]pyridine hydrochloride;
  7-[N-(2-chlorobenzoyl)-N-(4-fluorobenzyl)]amino-1,2,3-trimethyl-1H-pyrrolo[3,2-c]pyridine hydrochloride;
  7-[N-(4-fluorobenzyl)-N-phenoxycarbonyl]amino-1,2,3-trimethyl-1H-pyrrolo[3,2-c]pyridine hydrochloride;
  3-benzyl-2-methyl-4-(4-fluorobenzylamino)-1H-pyrrolo[3,2-c]pyridine hydrochloride;

3-benzyl-1,2-dimethyl-4-(4-fluorobenzylamino)-1H-pyrrolo[3,2-c]pyridine hydrochloride;
3-benzyl-2-methyl-4-(4-chlorobenzylamino)-1H-pyrrolo[3,2-c]pyridine hydrochloride; and
3-benzyl-1,2-dimethyl-4-(4-chlorobenzylamino)-1H-pyrrolo[3,2-c]pyridine hydrochloride.

4. A process for preparing a compound of formula (I) or a pharmaceutically acceptable salt thereof, which comprises:
(a) adding a sodium nitrite solution to a compound of formula (II), followed by reducing the resulting product with tin chloride, to obtain a compound of formula (III);
(b) reacting the compound of formula (III) with a compound of formula (IV) to obtain a compound of formula (V);
(c) performing a cyclization reaction of a compound of formula (V) to obtain a compound of formula (VI);
(d) halogenizing the compound of formula (VI) to obtain a compound of formula (VII);
(e) reacting the compound of formula (VII) with $R_4$—H to obtain a compound of formula (Ia); and
(f) reacting the compound of formula (Ia) with $R_1$—X to obtain a compound of formula (I):

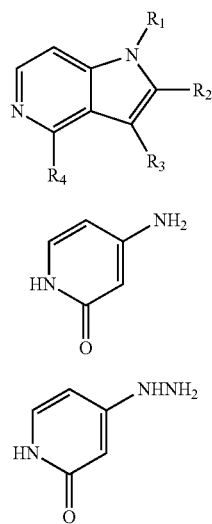

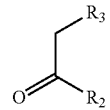

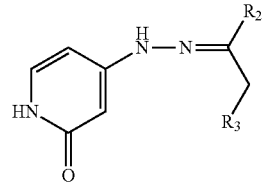

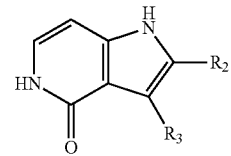

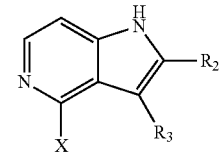

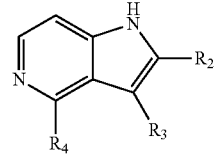

wherein, $R_1$, $R_2$, $R_3$, and $R_4$ are the same as defined in claim 1 and X is halogen.

5. A pharmaceutical composition comprising a therapeutically effective amount of any of the compound of formula (I) or a pharmaceutically acceptable salt thereof according to claim 1 and a pharmaceutically acceptable carrier.

* * * * *